US008852879B2

(12) United States Patent
Ischiropoulos

(10) Patent No.: US 8,852,879 B2
(45) Date of Patent: Oct. 7, 2014

(54) MATERIALS AND METHODS FOR THE DETECTION OF NITRATED FIBRINOGEN

(75) Inventor: Harry Ischiropoulos, Media, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 1325 days.

(21) Appl. No.: 12/168,739

(22) Filed: Jul. 7, 2008

(65) Prior Publication Data
US 2009/0048150 A1 Feb. 19, 2009

Related U.S. Application Data

(63) Continuation-in-part of application No. 11/118,851, filed on Apr. 29, 2005, now abandoned.

(60) Provisional application No. 60/566,555, filed on Apr. 29, 2004.

(51) Int. Cl.
C12Q 1/56 (2006.01)
G01N 33/543 (2006.01)
A61K 38/36 (2006.01)
A61K 45/06 (2006.01)
A61K 38/48 (2006.01)
G01N 33/86 (2006.01)
A61K 38/37 (2006.01)
G01N 33/68 (2006.01)
C07K 16/36 (2006.01)

(52) U.S. Cl.
CPC ............ *G01N 33/6893* (2013.01); *A61K 38/36* (2013.01); *G01N 2800/324* (2013.01); *A61K 45/06* (2013.01); *G01N 2800/52* (2013.01); *A61K 38/4846* (2013.01); *G01N 2800/50* (2013.01); *G01N 33/86* (2013.01); *A61K 38/4866* (2013.01); *A61K 38/37* (2013.01); *C07K 16/36* (2013.01); *A61K 38/363* (2013.01); *G01N 33/68* (2013.01); *G01N 2800/226* (2013.01); *G01N 33/543* (2013.01); *G01N 2333/75* (2013.01); *A61K 38/4833* (2013.01)
USPC ............................................ 435/13; 435/7.94

(58) Field of Classification Search
None
See application file for complete search history.

(56) References Cited

U.S. PATENT DOCUMENTS

| 4,208,479 | A | 6/1980 | Zuk et al. |
| 5,605,887 | A | 2/1997 | Pines et al. |
| 5,985,315 | A | 11/1999 | Patat et al. |
| 7,259,022 | B2 | 8/2007 | Comb et al. |
| 2002/0164662 | A1 | 11/2002 | Hazen et al. |
| 2005/0176081 | A1 | 8/2005 | Reginster et al. |

FOREIGN PATENT DOCUMENTS

| WO | 96/04311 | 2/1996 | |
| WO | WO 03/076946 A2 * | 9/2003 | ............. C07K 16/00 |

OTHER PUBLICATIONS

Shishehbor, M.H. "Association of Nitrotyrosine Levels With Cardiovascular Disease and Modulation by Statin Therapy"; JAMA, 289(13): 1675-1680 (2003).
Pignatelli, B. "Nitrated and Oxidized Plasma Proteins in Smokers and Lung Cancer Patients"; Cancer Research, 61: 778-784 (2001).
Gole, M.D. "Plasma proteins modified by tyrosine nitration in acute respiratory distress syndrome"; Am J Physiol Lung Cell Mol Physiol, 278: L961-L967 (2000).
Zhang, R. "Association Between Myeloperoxidase Levels and Risk of Coronary Artery Disease"; JAMA, 286(17): 2136-2142 (2001).
Vadseth, C. "Pro-thrombotic State Induced by Post-translational Modification of Fibrinogen by Reactive Nitrogen Species"; J Biol Chemistry, 279(10): 8820-8826 (2004).
Nowak, P. "Peroxynitrite-mediated modification of fibrinogen affects platelet aggregation and adhesion"; Platelets, 13:293-299 (2002).
Brennan, M.L. "A Tale of Two Controversies"; J Biol Chemistry, 277(20): 17415-17427 (2002).
Nicholls, S.J. "The Role of Myeloperoxidase in the Pathogenesis of Coronary Artery Disease"; Jpn. J. Infect. Dis., 57: S21-S22 (2004).
Turko, I.V. "Protein Nitration in Cardiovascular Diseases"; Pharmacol Rev, 54: 619-634 (2002).
Pennathur, S. "Human Atherosclerotic Intima and Blood of Patients with Established Coronary Artery Disease Contain High . . . "; J Biol Chemistry, 279(41): 42977-42983 (2004).
Khan, J. "3-Nitrotyrosine in the proteins of human plasma determined by an ELISA method"; Biochem. J., 330: 795-801 (1998).

(Continued)

Primary Examiner — Christine Foster
(74) Attorney, Agent, or Firm — Dann, Dorfman, Herrell & Skillman; Robert C. Netter, Jr.; Kathleen D. Rigaut

(57) ABSTRACT

Compositions are disclosed comprising an effective amount of nitrated fibrinogen and a pharmaceutically acceptable carrier for detecting a patient's risk for coronary artery disease. The compositions can be used to determine the presence of nitrated fibrinogen which is linked with coronary artery disease. Also disclosed is a method for determining the presence or risk for coronary artery disease or risk for increased propensity for an adverse thrombotic event in a patient. The method comprises obtaining a sample of blood or fraction thereof from a patient; determining by immunoassay the amount of nitrated fibrinogen in the sample based on binding of the nitrated fibrinogen to an antibody that specifically recognizes SEQ ID NO: 2 and/or SEQ ID NO: 3; and comparing the amount of the antibody-bound nitrated fibrinogen in the sample with the amount of nitrated fibrinogen in a sample from a normal individual, such that a greater amount of nitrated fibrinogen in the patient sample than in the normal individual indicates that the patient has or is at greater risk of coronary artery disease or risk of increased propensity for an adverse thrombotic event. Kits for performing the method which include the composition and aforementioned antibody or antibodies are also provided.

12 Claims, 20 Drawing Sheets

(56) References Cited

OTHER PUBLICATIONS

Pfeiffer, S. "Protein Tyrosine Nitration in Cytokine-activated Murine Macrophages"; J Biol Chemistry, 276(36): 34051-34058 (2001).
Pfeiffer, S. "Dityrosine Formation Outcompetes Tyrosine Nitration at Low Steady-state Concentrations of Peroxynitrite"; J Biol Chemistry, 275(9): 6346-6352 (2000).
"Thrombosis Prevention"; LifeExtension; Web pp. 1-22; http://www.lef.org/LEFCMS/aspx/PrintVersion Magic.aspx?CmsID=39979; (Updated Jul. 14, 2004).
Harlow, E. and Lane, D., "Antibodies: a laboratory manual," Cold Spring Harbor Press, Cold Spring Harbor, NY pp. 473, 499, and 612 (1988).

* cited by examiner

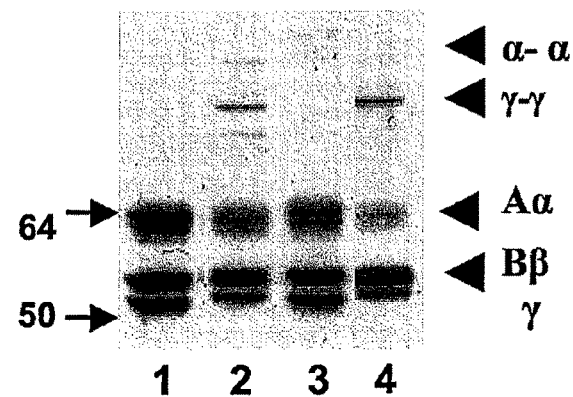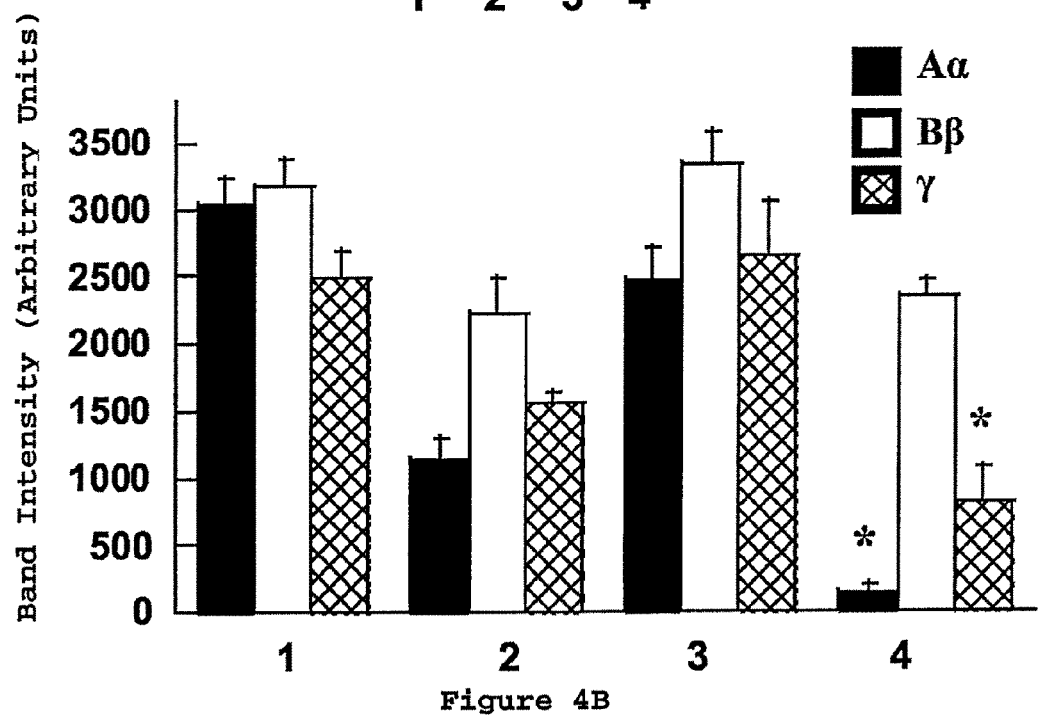

Figure 11
A
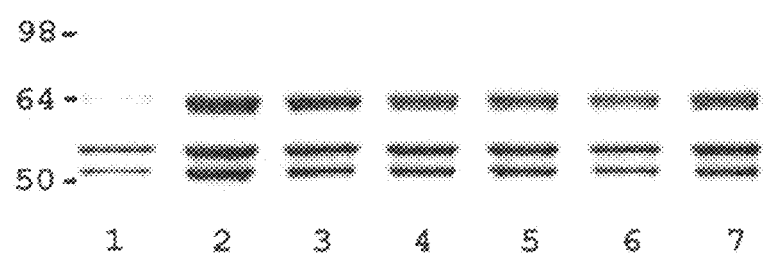
B
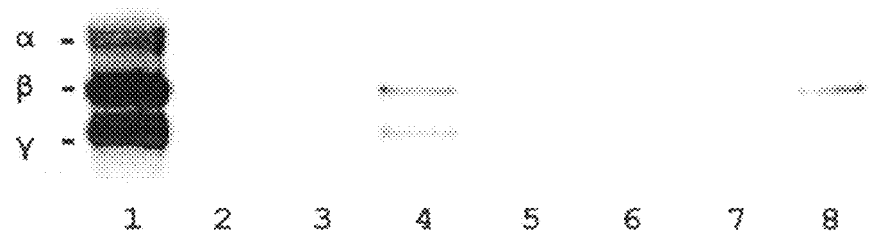

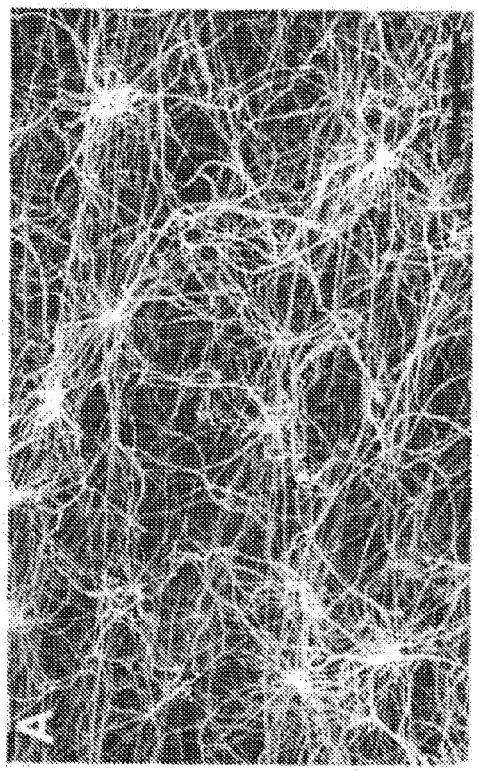
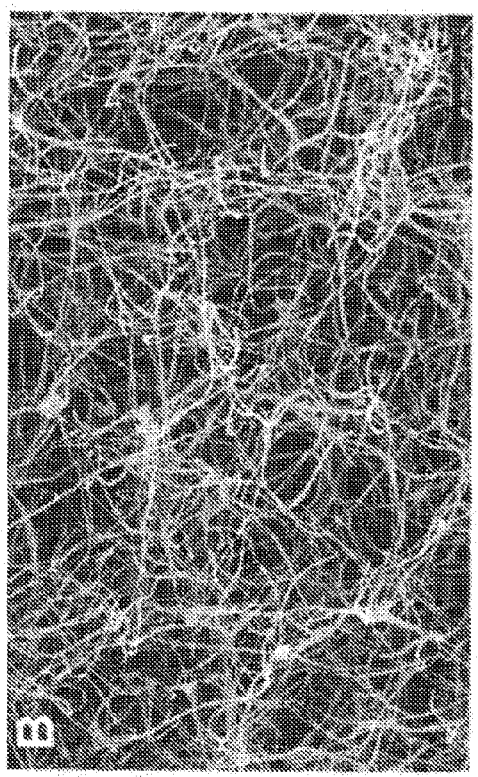
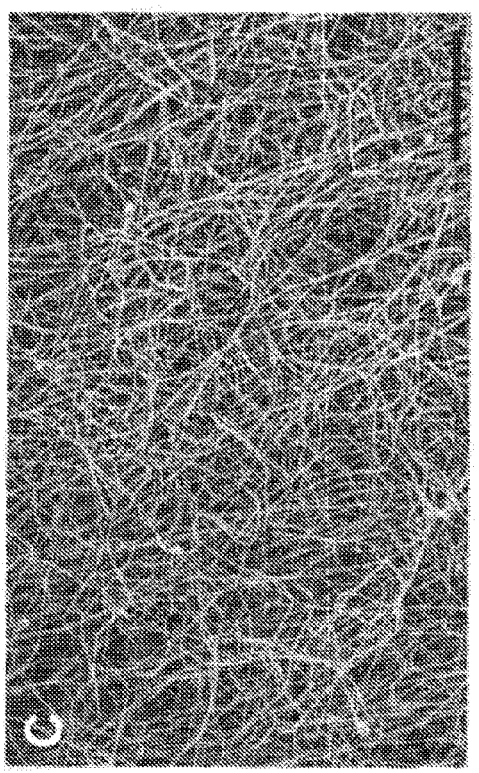
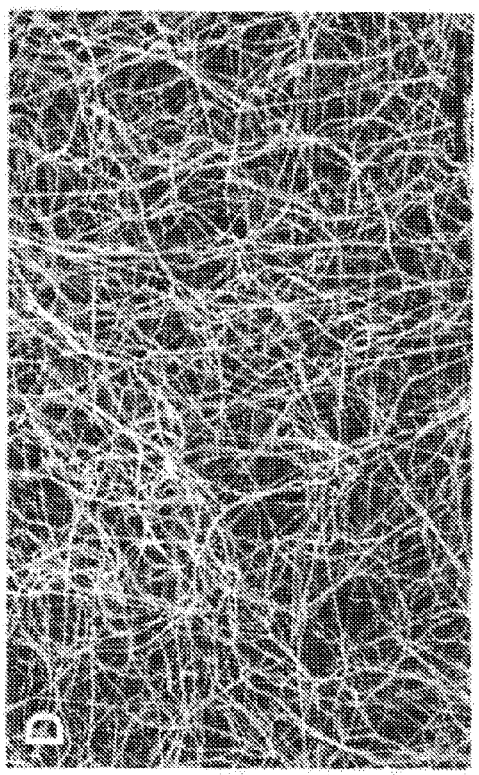
Figure 13

MATERIALS AND METHODS FOR THE DETECTION OF NITRATED FIBRINOGEN

This application is a continuation-in-part of U.S. application Ser. No. 11/118,851, filed on Apr. 29, 2005, now abandoned which claims priority under 35 U.S.C. §119(e) to U.S. Provisional Patent Application No. 60/566,555, filed on Apr. 29, 2004. The foregoing applications are incorporated by reference herein.

Pursuant to 35 U.S.C. Section 202(c), it is acknowledged that the United States Government has certain rights in the invention described herein, which was made in part with funds from the National Institutes of Health Grant No. P50-HL70128.

FIELD OF THE INVENTION

The present invention relates to methods for assessing patients for developing coronary artery disease. The instant invention also relates to methods of inducing blood clot formation.

BACKGROUND OF THE INVENTION

Several publications and patent documents are cited throughout the specification in order to describe the state of the art to which this invention pertains. Each of these citations is incorporated herein by reference as though set forth in full.

Epidemiological studies have suggested that increased levels of circulating fibrinogen provide an independent predictor of coronary heart disease and in some cases of premature death from cardiovascular disease, although a causative relationship between high levels of fibrinogen and cardiovascular disease has not been firmly established (Wilhelmsen et al. (1984) N. Engl. J. Med., 311:501-505; Kannel et al. (1987) J. Am. Med. Assoc., 258:1183-1186; Thompson et al. (1995) N. Engl. J. Med., 332:635-641; Salomaa et al. (1995) Circulation, 91:284-290).

Fibrinogen is a multifunctional protein essential for hemostasis. It is a 340-kDa glycoprotein, consisting of three non-identical peptide chains Aα, Bβ, and γ, which are linked together by 29 disulfide bonds (Weisel et al. (1985) Science, 230:1388-1391). During coagulation, soluble fibrinogen is converted to insoluble fibrin polymers. The process is initiated by thrombin, a serine protease, which initially catalyzes the cleavage of the two fibrinopeptides from the amino termini of the Aα chains and then two fibrinopeptides from the amino termini Bβ chains. Upon release of the fibrinopeptides, the remaining fibrin monomers aggregate spontaneously to form ordered fibrin polymers (Weisel et al. (1985) Science, 230:1388-1391). The clot is stabilized by the formation of covalent bonds introduced by the action of a transglutaminase, factor XIII (Murthy et al. (1999) Proc. Natl. Acad. Sci. U.S.A., 97:44-48). Under physiological conditions, fibrinolysis is dependent on the binding of circulating plasminogen and tissue-type plasminogen activator (tPA) to fibrin clots. Urokinase and tPA convert plasminogen to the active protease plasmin, which then cleaves fibrin polymers to soluble fragments completing the coagulation and clot resolution cycle.

A major cause of vascular injury leading to the development of atherosclerosis is oxidative stress (White et al. (1994) Proc. Natl. Acad. Sci. U.S.A., 91:1044-1048; Berliner et al. (1996) Free Radic. Biol. Med., 20:707-727; Diaz et al. (1997) N. Engl. J. Med., 337:408-416). Proteins are major targets for reactive species, and nitration of tyrosine residues is a selective protein modification induced by reactive nitrogen species in human disorders as well as animal and cellular models of disease (Ischiropoulos, H. (1998) Arch. Biochem. Biophys., 356:1-11; Turko and Murad (2002) Pharmacol. Rev., 54:619-634). Nitrated proteins have also been detected in atherosclerotic lesions (Beckman et al. (1994) Biol. Chem. Hoppe-Seyler, 375:81-88; Butter et al. (1996) Lab. Investig., 75:77-85; Baker et al. (1999) Arterioscler. Thromb. Vasc. Biol., 19:646-655; Leeuwenburgh et al. (1997) J. Biol. Chem., 272: 1433-1436; Cromheeke et al. (1999) Cardiovasc. Res., 43:744-754.

SUMMARY OF THE INVENTION

In one embodiment of the instant invention, methods for determining the presence or risk for coronary artery disease or risk for increased propensity for an adverse thrombotic event in a patient are provided. An exemplary method comprises 1) obtaining a sample of blood or fraction thereof from a patient; 2) determining the amount of nitrated fibrinogen in said sample; and 3) comparing the said amount of nitrated fibrinogen in said sample with the amount of nitrated fibrinogen in a sample from a normal individual. A greater amount of nitrated fibrinogen in said sample from said patient than in said normal individual is indicative of a greater risk or presence of coronary artery disease or risk of increased propensity for an adverse thrombotic event in said patient. An exemplary adverse thrombotic event is deep vein thrombosis for example. In accordance with this aspect, methods for determining the amount of nitrated fibrinogen include immunoassays. In another embodiment, the amount of nitrated fibrinogen is quantified by an ELISA. Particularly, a sandwich ELISA may be employed.

In another embodiment of the invention, an antibody or fragment thereof which has binding affinity for SEQ ID NO: 2 and/or SEQ ID NO: 3 are provided. Exemplary antibodies are selected from the group consisting of a monoclonal antibody, a polyclonal antibody, a diabody, an scFv, and functional fragments thereof.

In yet another embodiment of the invention, kits are provided for determining the presence or risk for coronary artery disease or risk for increased propensity for an adverse thrombotic event in a patient. An exemplary kit comprises at least one antibody having binding affinity for SEQ ID NO: 2 and/or 3, nitrated fibrinogen, non-nitrated or native fibrinogen, at least one antibody having binding affinity for native fibrinogen, said antibodies optionally comprising a detectable label, said kit optionally comprising containers for sample collection.

In another embodiment of the invention, a pharmaceutical composition comprising an effective amount of nitrated fibrinogen and a pharmaceutically acceptable carrier are provided. The pharmaceutical composition may further comprise one or more components selected from the group consisting of: a) one or more blood clotting factors; b) one or more stabilizers; c) one or more preservatives; and d) one or more antibiotics.

In still another embodiment, a method is provided for inducing blood clot formation at a wound site in a patient in need thereof, said method comprising administration of the pharmaceutical composition comprising an effective amount of nitrated fibrinogen and a pharmaceutically acceptable carrier.

BRIEF DESCRIPTION OF THE DRAWING

In FIG. 2A, the samples are reconstituted with 12 mM calcium. Tracings 1-3 represent different plasma samples from coronary artery disease patients, and tracings 4 and 5 are different control plasma samples. In FIG. 2B, the fibrinogen was exposed to 60 nM MPO plus 100 μM $H_2O_2$ and 100 μM $NO_2^-$ (tracing 1) and fibrinogen exposed to 60 nM MPO plus 100 μM $H_2O_2$ (tracing 2). In FIG. 2C, the fibrinogen was exposed to 100 μM SIN-1 (tracing 1), 100 μM SIN-1 in the presence of superoxide dismutase (tracing 2), and control fibrinogen (tracing 3). The inset is a graph representing the linear relationship between levels of in vitro nitration of fibrinogen and ratio of $V_0/A$ maximum. In FIG. 2D, the changes in fibrinogen turbidity were determined after addition of thrombin to fibrinogen that was exposed first to 100 μM SIN-1 and then oxidized by the addition of 100 μM HOCl (tracing 1) and to fibrinogen that was first oxidized by 100 μM HOCl and then exposed SIN-1 (tracing 2). Tracing 3 represents control fibrinogen and tracing 4 is fibrinogen exposed to 100 μM HOCl.

FIG. 4A is a Western blot of a control and fibrinogen exposed to 60 nM MPO plus 100 μM $H_2O_2$ and 100 μM $NO_2^-$, mixed with thrombin and factor XIII, and then separated and blotted with an anti-fibrinogen antibody. Lanes 1 and 3 are control and exposed fibrinogen, respectively, immediately after addition of thrombin and factor XIII. Lanes 2 and 4 are the corresponding fibrinogen 60 minutes after the addition of thrombin and factor XIII. FIG. 4B is a graph of the band intensity of the Aα, Bβ, and γ chains of fibrinogen which were quantified by densitometry. Values represent means±S.D. for three independent determinations. * indicates p<0.05 between the control and exposed fibrinogen after analysis of variance using Tukey's post hoc test.

DETAILED DESCRIPTION OF THE INVENTION

Figure 1A:
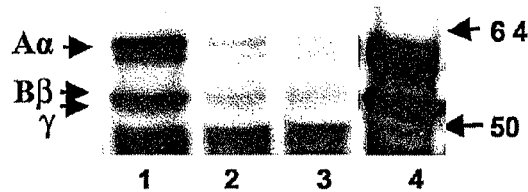
FIG. 1A is a Western blot of plasma proteins immunoprecipitated with affinity-purified monoclonal anti-nitrotyrosine proteins and detected with anti-fibrinogen antibodies. Lanes 1-3 are samples from three different patients with clinically documented coronary artery disease. Lane 4 is plasma from an age-matched control patient spiked with 20 ng of nitrated fibrinogen.
Figure 1B:
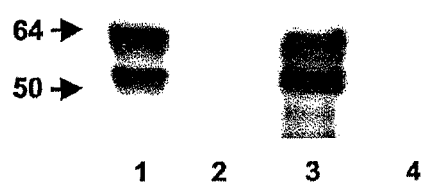
FIG. 1B is a Western blot of plasma from a coronary artery disease patient passed though an anti-fibrinogen polyclonal antibody column and detected by anti-fibrinogen monoclonal antibody. Lane 1 is the input plasma, lane 2 is the unbound fraction, lane 3 is the fibrinogen eluted from the column, and lane 4 is the fraction after fibrinogen elution.

The instant invention provides methods and kits for determining whether a patient has coronary artery disease or has an increase risk for developing coronary artery disease. The methods comprise obtaining a biological (e.g., blood) sample from a patient and determining the amount of nitrated fibrinogen, which is linked with coronary artery disease. For example, nitrated fibrinogen can be quantified by immunoprecipitating all of the fibrinogen from a sample with an antibody specific for fibrinogen and subsequently performing biochemical analyses on the isolated fibrinogen to determine the amount that is nitrated. Such biochemical analyses may include, for example, hydrolysis, high performance liquid chromatography, and/or mass spectrometry. In a preferred embodiment, immunoassays such as Western blotting, ELISAs (direct, indirect, and sandwich), radio-immunoassays, and immunofluorescence assays are employed to quantify the amount of nitrated fibrinogen in a sample. The presence of a greater amount of nitrated fibrinogen or greater ratio of nitrated fibrinogen to fibrinogen in the sample from the patient than from the normal individual indicates the presence of coronary artery disease or a greater risk thereof.

The instant invention also provided methods and kits, centered around the administration of nitrated fibrinogen, for rapidly inducing the formation of blood clots.

I. DEFINITIONS

As used herein, the phrase "coronary artery disease" generally refers to any disease of arteries that supply blood to the heart and/or arteries that surround the heart. More specifically, coronary artery disease refers to disorders and conditions generally recognized by those skilled in the art as related to the deposition of atheroma in the large- and medium-sized arteries serving the heart. Typically, coronary artery disease is caused by gradual blockage of the coronary arteries. One of skill in the art realizes that in typical coronary artery disease, atherosclerosis (i.e., "hardening of the arteries") causes thick patches (i.e., plaque) of fatty tissue to form on the inside of the walls of the coronary arteries. As the plaque thickens, the artery narrows and blood flow decreases, which results in a decrease in oxygen to the myocardium. This decrease in blood flow precipitates a series of consequences for the myocardium. Coronary artery disease may also refer to clinical syndromes which are based on the pathology of coronary artery atheroma. Clinical syndromes include, without limitation, angina, myocardial infarction, unstable angina, and sudden ischemic death. For example, the term "coronary artery disease" includes thrombosis or a blood clot in the coronary arteries.

The term "fibrinogen" without more is intended to include any type of fibrinogen. Fibrinogen, therefore, refers to monomeric and dimeric fibrinogen molecules having the monomer structure (AαBβγ), hybrid molecules, and variants thereof, whether naturally occurring, modified, or synthetic. The term "fibrinogen" refers generally to fibrinogen from humans, but may include fibrinogen of any species, especially mammalian species. Amino acid and nucleotide sequences of fibrinogen are available at GenBank.

As used herein, the term "immunoassay" refers to any assay that uses at least one specific antibody for the detection and/or quantification of an antigen. Immunoassays include, but are not limited to, Western blots, ELISAs, radio-immunoassays, and immunofluorescence assays.

"ELISA" refers to an enzyme-linked immunosorbent assay that, in general, employs an antibody or antigen bound to a solid phase and a detectably labeled-antigen or detection antibody to detect and/or quantify the amount of an antigen or antibody present in a sample. Typically, the detectably labeled-antigen or detection antibody is an enzyme-conjugated antigen or enzyme-conjugated antibody. Numerous ELISA methods and applications are known in the art (see, e.g., Crowther, "Enzyme-Linked Immunosorbent Assay (ELISA)," in *Molecular Biomethods Handbook*, Rapley et al. [eds.], pp. 595-617, Humana Press, Inc., Totowa, N.J., 1998; Harlow and Lane (eds.), *Antibodies: A Laboratory Manual*, Cold Spring Harbor Laboratory Press, 1988; Ausubel et al. (eds.), *Current Protocols in Molecular Biology*, Ch. 11, John Wiley & Sons, Inc., New York, 1994). In addition, there are numerous commercially available ELISA test systems.

As used herein, a "direct ELISA" refers to an ELISA wherein an antigen in a sample is detected. For example, a sample containing an antigen is exposed to a solid support, the antigen is immobilized on the solid support, and the antigen is detected directly using a detection antibody specific for the antigen. Alternatively, an antibody in a sample can be detected by immobilization on a solid support and directly detected using a detectably-labeled antigen specific for the antibody.

As used herein, an "indirect ELISA" may refer to an ELISA wherein an antigen is immobilized on a solid support as in the direct ELISA, but is detected indirectly by first adding an antigen-specific antibody, followed by the addition of a detection antibody (e.g., "species-specific" antibodies such as a goat anti-rabbit antibody) specific for the antigen-specific antibody.

As used herein, the term "sandwich ELISA" refers to an ELISA wherein the antigen is immobilized on a solid support via an antibody (i.e., a capture antibody) which is immobilized on the solid support and is able to bind the antigen. For example, following the affixing of a suitable capture antibody to the solid support, a sample may then be added to the solid support such that antigens present in the sample are bound to the capture antibody present on the solid support. The solid support typically is washed to remove undesired compounds and blocked with non-relevant protein such as albumin. Subsequently, the captured antigen may be detected directly by using a detection antibody directed against the antigen. Alternatively, the captured antigen is detected indirectly by using an antibody directed against the antigen, which is then detected by a detection antibody which binds the antigen-specific antibody (leading to the formation of an antibody-antigen-antibody-antibody complex). Notably, there is no limit on the number of additional antibodies added in order to detect the antigen-antibody complex.

As used herein, the term "capture antibody" refers to an antibody that is used (e.g., in a sandwich ELISA) to bind (i.e., capture) an antigen in a sample prior to detection of the antigen. For example and without limitation, biotinylated capture antibodies may be captured on an avidin-coated solid support. Other methods of immobilizing a capture antibody on a solid support are well known in the art.

As used herein, a "detection antibody" is an antibody which carries a detectable label for visualization and/or quantification. Examples of detectable labels include, without limitation: biotin, avidin, fluorescent compound, a radioisotope, and an enzyme. Typically, the detectable label is a conjugated enzyme moiety that typically yields a colored or fluorescent reaction product following the addition of a suitable substrate. Conjugated enzymes commonly used with detection antibodies in the ELISA include, without limitation, horseradish peroxidase, urease, alkaline phosphatase, glucoamylase, and β-galactosidase.

As used herein, the term "amplifier" is used in reference to a system or compound which enhances the signal in a detection method.

As used herein, the term "solid support" refers to any solid or stationary material to which reagents such as antibodies, antigens, and other test components can be attached. Examples of solid supports include, without limitation, microtiter plates (or dish), microscope (e.g. glass) slides, coverslips, beads, cell culture flasks, chips (for example, silica-based, glass, or gold chip), membranes, particles (typically solid; for example, agarose, SEPHAROSE® (gel filtration medium), polystyrene or magnetic beads), columns (or column materials), and test tubes. Typically, the solid supports are water insoluble.

The term "kit" refers to a combination of reagents and other materials.

As used herein, an "instructional material" includes a publication, a recording, a diagram, or any other medium of expression which can be used to communicate the usefulness of the compositions of the invention for performing a method of the invention.

As used herein, "bleeding disorder" refers to the decreased ability to control bleeding.

The term "effective amount" includes reference to a dosage of an agent sufficient to produce a desired result, such as increasing blood clotting.

The term "pharmaceutically acceptable carrier" includes any and all solvents, dispersion media and the like which may be appropriate for the desired route of administration of the pharmaceutical composition. The use of such media for pharmaceutically active substances is known in the art. Except insofar as any conventional media or agent is incompatible with the compounds to be administered, its use in the pharmaceutical preparation is contemplated. Examples of pharmaceutically acceptable carriers include, without limitation, water, buffered saline, ethanol, polyol (for example, glycerol, propylene glycol, liquid polyethylene glycol and the like), dimethyl sulfoxide (DMSO), oils, detergents, suspending agents or suitable mixtures thereof. Suitable pharmaceutically acceptable carriers and formulations are described in Remington's Pharmaceutical Sciences, 19th Ed. (Mack Publishing Co., Easton, 1995).

The term "stabilizer" refers to a chemical agent (e.g., protein or polysaccharide) that assists to preserve or maintain the biological structure and/or biological activity of a protein. Examples of stabilizers include, without limitation, hydroxyethyl starch (hetastarch), serum albumin, gelatin, collagen, recombinant albumin, recombinant gelatin, recombinant collagen, non-oxidizing amino acid derivatives (e.g., tryptophan derivatives, such as N-acetyl-tryptophan), caprylates, polysorbates, amino acids, and divalent metal cations (e.g., $Zn^{2+}$), and cresols.

The term "antibiotics" refers to, without limitation, β-lactams (penicillins and cephalosporins), vancomycins, bacitracins, macrolides (erythromycins), lincosamides (clindomycin), chloramphenicols, tetracyclines (e.g., immunocycline, chlortetracycline, oxytetracycline, demeclocycline, methacycline, doxycycline and minocycline), aminoglycosides (e.g., gentamicins, amikacins, and neomycins), amphotericns, cefazolins, clindamycins, mupirocins, sulfonamides and trimethoprim, rifampicins, metronidazoles, quinolones, novobiocins, polymixins and gramicidins and the like and any salts or variants thereof.

An "antibody" or "antibody molecule" is any immunoglobulin (e.g., IgG, IgM, IgA, IgE, IgD, etc.), including antibodies and fragments thereof, that binds to a specific antigen. The term includes polyclonal, monoclonal, chimeric, and bispecific antibodies. As used herein, antibody or antibody molecule includes recombinantly generated intact immunoglobulin molecules and immunologically active portions of an immunoglobulin molecule such as, without limitation: Fab, Fab', $F(ab')_2$, F(v), scFv, $scFv_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668). An antibody can be obtained from any source such as, without limitation, humans, rodents, non-human primates, lagomorphs, caprines, bovines, equines, and ovines. Methods for recombinantly producing antibodies are well-known in the art. For example, commercial vectors comprising constant genes to make IgGs from scFvs are provided by Lonza Biologics (Slough, United Kingdom).

The phrase "specifically recognizes", as used herein, refers to the binding affinity demonstrated by an antibody for its cognate antigen. The skilled artisan is aware of the many methods available to measure the binding affinity of an antibody for an antigen (see, e.g., *Antibodies, A Laboratory Manual*, (1988) Cold Spring Harbor Publications, New York). Preferably, the antibody demonstrates binding affinity for the protein(s) of interest to the exclusion of other proteins.

As used herein, the phrase "test subject" refers to any animal, such as a human or a mammal.

"Fv" is an antibody fragment which contains an antigen-recognition-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

As used herein, the term "monoclonal antibody" or "mAb" refers to any essentially homogeneous antibody or antigen-binding region thereof that is reactive with, preferably specifically reactive with, a single epitope (antigenic determinant). The term "monoclonal antibody" may refer to generally homogeneous antibodies that are native, modified, or synthetic, and can include hybrid or chimeric antibodies. Typically, monoclonal antibodies are derived from a single clone of B lymphocytes (i.e., B cells). Monoclonal antibodies may be produced by methods known in the art.

A "polyclonal antibody" is a group of heterogeneous antibodies that recognize epitopes or antigenic determinants present on a protein. Typically, polyclonal antibodies originate from many different clones of antibody-producing cells.

The term "antigen-binding region" refers to a naturally occurring, modified, or synthetic fragment of an antibody of the invention that is reactive with an epitope. Such antigen-binding regions include, but are not limited to, Fab, F(ab')$_2$, and Fv fragments.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

II. PREPARATION OF ANTIBODY MOLECULES

For the production of antibodies, various host animals may be immunized by injection with the protein of interest, e.g., nitrated fibrinogen and/or fragments thereof. Such host animals include, without limitation, rabbits, mice, goats, and rats. Those of skill in the art are well apprised of the various adjuvants which may be employed to increase antibody titer obtained from the host. Common adjuvants include, without limitation, Freund's adjuvant, Ribi adjuvant, and the like.

Other methods of increasing antibody production are known to those skilled in the art in supplement or in lieu of the use of adjuvants.

Methods for obtaining polyclonal sera (antibodies) and monoclonal antibodies are well known in the art (see, in general, Ausubel et al. (eds.), Current Protocols in Molecular Biology, John Wiley & Sons, Inc., New York, 1994); Coligan, Current Protocols in Immunology, Wiley/Greene, New York (1991); and Harlow and Lane (1988) Antibodies, A Laboratory Manual, Cold Spring Harbor Publications, New York). Other techniques are taught by Kohler and Milstein (Nature (1975) 256:495-497); Mayer and Walker (Immunochemical Methods in Cell and Molecular Biology, (1987) Academic Press, London); U.S. Pat. No. 4,376,110; Kosbor et al. (Immunol. Today (1983) 4:72); Cole et al. (Proc. Natl. Acad. Sci. USA (1983) 80:2026-2030); Cole et al. (Monoclonal Antibodies And Cancer Therapy (1985) Alan R. Liss, Inc., pp. 77-96).

The antibody molecules of the invention may be prepared using any method known in the art. Antibodies may be prepared by chemical cross-linking, chimeric antibody technology, hybrid hybridoma techniques, and by expression of recombinant antibody fragments expressed in host cells, such as, without limitation, bacteria or yeast cells.

The antibody molecules may also be produced by expression of recombinant antibody fragments in host cells. The resulting antibody molecules may then be isolated and purified from the expression system. The antibodies optionally comprise a purification tag to facilitate purification of the antibody.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

III. KITS FOR THE DIAGNOSIS OF CORONARY ARTERY DISEASE

Kits of the instant invention may be employed for the detection of coronary artery disease in a patient or the increased likelihood of coronary artery disease in a patient. An exemplary kit comprises an antibody having specific binding affinity for nitrated fibrinogen and reagents for performing an immunoassay. The kit may comprise one or more of the following: capture antibodies, detection antibodies, positive and/or negative controls (e.g., nitrated fibrinogen, fibrinogen, and nitrated proteins which are not fibrinogen), detection reagents, and amplifiers. In a particular embodiment, the positive control is a composition comprising nitrated fibrinogen at a concentration consistent with (i.e., equal to) the concentration of nitrated fibrinogen in a sample from a normal individual (i.e. one not suffering from coronary artery disease). Other kit components include, without limitation, one or more of the following: apparatus for sample collection, sample tubes, solid supports, instruction material, and other solutions or other chemical reagents.

IV. SCREENING METHODS

The methods described herein for the diagnosis of coronary artery disease or the risk thereof may also be employed in a screening method for identifying compositions or compounds which decrease the risk of coronary artery disease or ameliorate the symptoms of coronary artery disease. Briefly, the screening method may comprise the administration of at least one test compound (e.g., chemical, natural product, protein, enzyme, nucleic acid molecule) to a patient or an animal. After the passage of a sufficient amount of time to allow the compound(s) to be efficacious, a blood sample is obtained. The amount of nitrated fibrinogen is then determined both pre- and post-administration of the test compound. A reduction in the amount of nitrated fibrinogen (or ratio of nitrated fibrinogen/fibrinogen) indicates the test compound has efficacy in the treatment of coronary artery disease or is effective to lower the risk of developing coronary artery disease. As an example, the test compounds may be compounds suspected of inhibiting the activity of proteins responsible for the nitration of fibrinogen. Additionally, the patient or animal can be monitored multiple times over the course of a study and the test composition may be administered more than once, as desired (e.g., to maintain bloodstream levels). The samples obtained from the test patient or animal may be compared to other samples from the test patient or animal and/or samples from one or more control patients or animals (positive or negative) not receiving the test composition.

V. BLOT CLOTTING

Blood loss resulting from trauma is a leading cause of mortality. Fibrinogen is the building block of a fibrin clot, the body's natural defense against bleeding. Thrombin removes two small fibrinopeptides from fibrinogen and the removal of these two small peptides allows the fibrin monomers to come together and form fibrin polymers. Formation of the fibrin polymers constitutes the first and critical step in the formation of a fibrin clot. Therefore, having available a natural protein, namely nitrated fibrinogen, which can form a clot significantly faster than normal is an enormous help to rapidly initiate the clotting cascade and stop bleeding from wound sites.

In light of its rapid clot forming abilities, the application of pharmaceutical compositions comprising modified fibrinogen would be very useful in hospital, rural, and battlefield setting, where rapid clotting may be necessary (e.g., during hemorrhaging). Indeed, pharmaceutical compositions comprising modified fibrinogen can be used, without limitation, during surgery, postoperative bleeding episodes, clinical procedures, and dental procedures, particularly for high risk individuals. Pharmaceutical compositions comprising nitrated fibrinogen may also be employed for effective treatment of, without limitation, burns, bleeding disorders (e.g., hemophilia), and septic syndromes.

Pharmaceutical compositions of the invention comprise an effective amount of nitrated fibrinogen in a pharmaceutically acceptable carrier. The pharmaceutical compositions of the instant invention are effective to cause hemostasis (i.e., arrest of bleeding), wound sealing, blood clotting, decrease of blood loss, and/or help effect blood coagulation. The pharmaceutical compositions may further comprise one or more blood clotting factor such as, without limitations, Factor VII, Factor VIIa, fibrinogen, prothrombin, thrombin, Factor VIII, Factor IX, Factor X, Factor XIII, vitamin-K dependent procoagulent, and protein C (see, e.g., U.S. Pat. No. 6,825,323). The blood clotting factors may be natural or modified to have superior qualities. As an alternative, the other blood clotting factors may be administered separately in other pharmcauetical compositions (i.e., before, simultaneously, or after administration of the nitrated fibrinogen). The pharmaceutical compositions of the instant invention may also comprise stabilizers to promote the longevity of the components (e.g., nitrated fibrinogen) as well as preservatives (e.g., anti-microbial agents, benzyl alcohol, benzoic acid, phenol, parabens, and sorbic acid) to inhibit contamination. The pharmaceutical compositions may also comprise antibiotics to help prevent infections of the wound site.

The pharmaceutical compositions of the instant invention may be administered via a carrier. For example, the pharmaceutical compositions may be in a stent, coated on a stent, applied to (e.g., coating) a medical dressing (e.g., without limitation, a bandages, gauzes, and sponges). Alternatively, the pharmaceutical compositions may be administered directly to the site or nearby blood vessels by injection.

Furthermore, the pharmaceutical compositions of the instant invention may be provided as part of a kit. For example, a kit for rapid blood clotting may comprise a pharmaceutical composition comprising nitrated fibrinogen as described hereinabove. The pharmaceutical composition comprising nitrated fibrinogen may further comprise other blood clotting factors or said other blood clotting factors may be provided in separate containers. The kits may also include one or more other items or materials which would be desirable for blood clotting such as, without limitation, any excipient or device (e.g., syringe) required for administration of the pharmaceutical composition(s), wound cleaning agents (e.g. alcohol, saline, and means of irrigation (e.g., squirt bottle))), tourniquets, medical dressings, pain killers (e.g., analgesics such as narcotic analgesics (e.g., morphine); non-narcotic analgesics (e.g., aspirin and acetaminophen); and narcotic antagonistic analgesics), and antibiotics.

The following examples are provided to illustrate various embodiments of the present invention. They are not intended to limit the invention in any way.

EXAMPLE I

Materials and Methods

Human Studies—Sequential patients presenting to the Cardiology Section of the Cleveland Clinic Foundation or responding to local advertisements were enrolled. To be classified as having coronary artery disease, patients had to have a documented history of myocardial infarction, coronary artery bypass graft surgery, percutaneous coronary intervention, or a stenosis of 50% or greater in one or more major coronary vessels demonstrated by coronary angiography. To be considered a control, subjects had to have no clinical history of coronary artery disease, no known peripheral artery disease, or history of symptoms suggestive of angina pectoris or congestive heart failure. All patients gave written, informed consent, and the Institutional Review Board of the Cleveland Clinic Foundation approved the study protocol.

Immunoprecipitation—Human plasma (225 µg) was precleared with Protein G SEPHAROSE® (medium for purification of antibodies) fast flow beads (Amersham Biosciences; Piscataway, N.J.) in lysis buffer (20 mM Tris, 150 mM NaCl, 10% glycerol, 1.0% Triton X-100, 4.0 mM EGTA) containing a protease inhibitor mixture (Sigma; St. Louis, Mo.) for 1 hour at 4° C. in order to remove the nonspecific proteins. The mixture was centrifuged for 3 minutes at 13,000 rpm, and 40 µg of monoclonal anti-nitrotyrosine antibody (Gole et al. (2000) Am. J. Physiol., 278:L961-L967) was added to the supernatant and incubated overnight at 4° C. while rotating. The samples were then incubated at 4° C. for 1 hour with Protein G SEPHAROSE® while rotating and then centrifuged at 13,000 rpm for 3 minutes. The beads were washed three times for 2 minutes each with freshly prepared lysis buffer containing the protease inhibitor mixture. The samples were pelleted by centrifugation for 3 minutes at 13,000 rpm, and 30 µl of 2× sample buffer containing SDS and 2-mercaptoethanol was added to the pellet. The beads were boiled for 10 minutes and centrifuged at 13,000 rpm for 3 minutes, and the supernatant was then analyzed by SDS-electrophoresis. The proteins were separated on 6% SDS-PAGE and transferred to nitrocellulose paper (Schleicher & Schuell; Keene, N.H.). The blot was blocked with dry milk solution and then incubated with rabbit anti-human fibrinogen-horseradish peroxidase-conjugated antibody (Dako Corp.; Carpinteria, Calif.). After antibody incubation, the blot was developed with ECL Western blotting detection reagent (Amersham Biosciences).

Affinity Purification of Fibrinogen from Human Subjects Plasma—An ImmunoPure Protein A IgG Orientation Kit (Pierce; Rockford, Ill.) was utilized to affinity-purify fibrinogen from coronary artery disease and age-matched control patient plasma. Briefly, rabbit anti-human fibrinogen antibody (Dako Corp.) was bound to protein A and cross-linked with dimethylpimelimidate. For sample application, the patient plasma was diluted in 10 mM Tris, pH 7.5, and applied to the column. Unbound protein fractions were eluted with 10 mM Tris, pH 7.5. Fractions of bound fibrinogen were eluted with 100 mM glycine-HCl, pH 2.8, and collected in tubes containing 1 M Tris-HCl, pH 8.0. All fractions were dried down to a small volume using a Savant Instrument SpeedVac Concentrator (Savant Instruments Inc.; Holbrook, N.Y.). Protein in the fractions was monitored by absorbance at 280 nm. All fractions containing antigen or unbound protein were pooled together, respectively, and analyzed by SDS-PAGE as described above. Nitrotyrosine levels were determined by HPLC with on-line electrospray ionization/tandem mass spectrometry using stable isotope dilution methodology and an ion trap mass spectrometer, as described previously (Shishehbor et al. (2003) J. Am. Med. Assoc., 289:1675-1680; Brennan et al. (2002) J. Biol. Chem., 277:17415-17427).

Nitration and Oxidation of Fibrinogen—Freeze-dried human fibrinogen (American Diagnostica, Inc.; Greenwich, Conn.), which was free of plasminogen, factor XIII, and fibronectin, with coagulability greater than 95%, was solubilized in filtered de-ionized water. The fibrinogen solution was then eluted through a PD-10 desalting column (Amersham Biosciences). Stock fibrinogen solutions were divided equally into two tubes, and an equal volume of buffer (100 mM potassium phosphate buffer, 50 mM sodium bicarbonate, pH 7.4) was added to each tube. Fibrinogen was exposed to 60 nM myeloperoxidase (MPO) plus 100 µM $H_2O_2$ in the absence or presence of 100 µM nitrite for 1 hour. In the absence of nitrite and in physiological concentrations of chloride, MPO catalyzes the formation of hypochlorous acid (HOCl), a strong oxidant and chlorinating agent. In the presence of nitrite in addition to HOCl, MPO also catalyzes the formation of nitrogen dioxide, an oxidant and nitrating agent (Brennan et al. (2002) J. Biol. Chem., 277:17415-17427; Baldus et al. (2001) J. Clin. Investig., 108:1759-1770; Gaut et al. (2002) J. Clin. Investig., 109:1311-1319). As a control, fibrinogen was also exposed to 100 µM reagent HOCl. Fibrinogen was also exposed to 3-morpholinosydnonimine, HCl (SIN-1) (Calbiochem-Novabiochem; La Jolla, Calif.). SIN-1 is dissolved in 50 mM potassium phosphate buffer, pH 5.0, and purged with nitrogen gas before and after each use. SIN-1 undergoes base hydrolysis to release nitric oxide and superoxide in solution (for 100 µM SIN-1 the rate is 1 µM per minute), which they react with a rate constant of $10^{10} M^{-1} s^{-1}$ to form peroxynitrite. The samples were incubated at 37° C. for 1 hour, which is approximately twice the half-life of SIN-1, and vortexed every 10 minutes to preserve the dissolved oxygen levels in the mixture. As a control, fibrinogen was exposed to SIN-1 in the presence of Cu,Zn superoxide dismutase (Calbiochem-Novabiochem) at 0.3 mg/ml to compete nitric oxide for superoxide. Under these conditions, fibrinogen is exposed to nitric oxide plus $H_2O_2$.

After incubation with the different chemical systems, the samples were applied to a PD-10 desalting column and were eluted with TBS (50 mM Tris base, 150 mM sodium chloride, pH 7.4). Following the different exposures, the nitration of fibrinogen was confirmed by Western blotting with anti-nitrotyrosine antibodies and by liquid chromatography/electrospray ionization/mass spectrometry analysis (Table I), whereas oxidation was assessed by the formation of carbonyls (Table I) as described previously (Shacter et al. (1995) Free Radic. Biol. Med., 18:815-821). Western blotting confirmed that exposure to SIN-1 and MPO/$H_2O_2$/$NO_2^-$ but not in the other controls results in nitration of tyrosine residue(s) in all three fibrinogen chains. The nitration of fibrinogen did not result in any significant change in fibrinogen structure as determined by the CD spectrum of the control and nitrated fibrinogen. Under the experimental conditions, exposure of fibrinogen to either SIN-1 or MPO/$H_2O_2$/$NO_2^-$ did not result in covalent protein cross-linking.

Thrombin-catalyzed Fibrin Clot Polymerization—Polymerization was initiated by the addition of 0.1 unit/ml of human thrombin (American Diagnostica Inc.) to fibrinogen (1 mg/ml) in TBS, pH 7.4 (50 mM Tris base, 150 mM sodium chloride). Clot formation was monitored at 25° C. as the increase in absorbance at 350 nm over time using a Hewlett-Packard diode array spectrophotometer. Clot formation in human plasma samples was initiated by simultaneous addition of $CaCl_2$ (12 mM final concentration) and rabbit brain thromboplastin (Plastinex® from Bio/Data Co.; Horsham, Pa.). The concentration of thromboplastin in plasma was 1.4 mM relative to stock. Turbidity was measured in glass cells with a 1-mm optical path length. The formation of fibrinopeptides A and B after addition of thrombin was followed over time by HPLC separation and UV detection. Factor XIII fibrinogen and fibrin cross-linking was performed as described previously (Weisel and Nagaswami (1992) Biophys. J., 63:111-128).

Scanning Electron Microscopy—Fibrin clots made at room temperature using 0.1 unit/ml thrombin were processed for scanning electron microscopy as described previously (Weisel and Nagaswami). All samples were prepared at least in duplicates, and for all clots at least three high resolution images from different regions were obtained.

Permeation and Viscoelastic Measurements—The Darcy constant, which represents the surface of the gel allowing flow through a network, and thus provides information on the pore structure and fiber diameter, was calculated from the flow measurements, pressure, and geometric parameters of the clot as described in detail previously (Ryan et al. (1999) Biophys. J., 77:2813-2826). Viscoelastic measurements were performed in clots prepared between 12-mm diameter glass coverslips in a Plazek torsion pendulum described above for permeation studies (Ryan et al.). Each clot was measured three times, and three clots were prepared for each sample on 2 different days.

Lysis of Fibrin Clot—Clot lysis by 6 nM of recombinant tPA (American Diagnostica) was monitored as described (Veklich et al. (1998) Blood, 92:4721-4729; Collet et al. (2000) Arterioscler. Thromb. Vasc. Biol., 20:1354-1361). The percent lysis was calculated after adjusting for value of the starting absorbance. The plasmin protection assay and the plasmin digestion of fibrin clots were performed as described previously (Veklich et al.). The previous published protocols for the preparation and lysis of $^{125}$I-fibrin microparticles was utilized as described in detail previously (Murciano et al. (2002) Am. J. Physiol., 282:L529-L539; Bdeir et al. (2000) Blood, 96:1820-1826).

Platelet Aggregation and Adhesion—Aggregation of gel-filtered platelets was measured on a Dual Channel Aggregometer (Chrono-log Corp.; Havertown, Pa.) in the presence of 150 µg/ml fibrinogen, 0.5 mM $CaCl_2$, and different concentrations of ADP varying from 2 to 20 µM (Belisario et al. (1997) Biochimie (Paris), 79:449-455). For platelet adherence to control and nitrated fibrinogen Immulon 2HB microtiter plates were employed, and adherence was measured by the phosphatase assay (Bennett and Vilaire (1979) J. Clin. Investig., 64:1393-1401) utilizing a universal microplate reader (Bio-Tek Instruments, Inc.; Winooski, Vt.).

Results

Figure 1C:
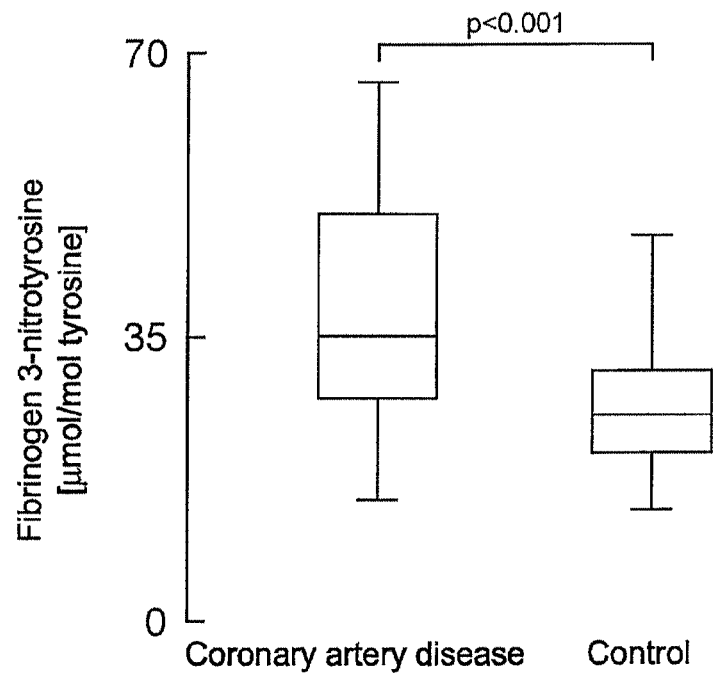
FIG. 1C is a graph of 3-nitrotyrosine in affinity-purified fibrinogen from age- and gender-matched control (n=26) and coronary artery disease (n=30) patient plasma. Box-whisker plots of 3-nitrotyrosine levels in fibrinogen versus coronary artery disease status. The boxes encompass the 25th and 75th percentiles and lines within boxes represent median values. Bars represent the 2.5th and 97.5th percentiles.

Detection of Nitrated Fibrinogen in Patients with Coronary Artery Disease—Plasma proteins from coronary artery disease patients were immunoprecipitated with a monoclonal anti-nitrotyrosine antibody. Probing the immunoprecipitated proteins with a polyclonal anti-fibrinogen antibody revealed that a fraction of fibrinogen was nitrated in coronary artery disease patient plasma (FIG. 1A). In order to confirm and quantify the presence of nitrated fibrinogen in coronary artery disease and age-matched control patient plasma, fibrinogen was purified using affinity chromatography in which the Fc portion of a polyclonal anti-fibrinogen antibody was coupled to protein A. The ability of the anti-fibrinogen column to capture nitrated fibrinogen was confirmed by using in vitro nitrated fibrinogen. The affinity column was efficient in capturing all the fibrinogen for the input plasma (FIG. 1A). The eluted fibrinogen was then hydrolyzed in order to quantify the protein 3-nitrotyrosine levels by HPLC with on-line electrospray ionization/tandem mass spectrometry using stable isotope dilution methodology and an ion trap mass spectrometer (Shishehbor et al. (2003) J. Am. Med. Assoc., 289:1675-1680; Brennan et al. (2002) J. Biol. Chem., 277:17415-17427). The values were normalized to the levels of tyrosine to avoid changes in fibrinogen levels among patients. A 30% increase (p<0.001) in the levels of nitrated fibrinogen was found in coronary artery disease patients (n=30) as compared with age-matched controls (n=26) (FIG. 1C).

Effect of Fibrinogen Nitration on Fibrin Clot Formation—The polymerization of fibrin catalyzed by thrombin monitored by changes in turbidity at 350 nm in human plasma after the addition of 12 mM calcium from coronary artery disease patients and controls is depicted in FIG. 2A. The thrombin-induced polymerization of fibrinogen recovered from patients with coronary artery disease showed a shorter lag phase, a rapid rise in the initial velocity, and increased final turbidity as compared with fibrinogen recovered from plasma of controls. The changes in fibrinogen polymerization were not due to fibrinogen concentration in plasma since the mole content of tyrosine in the purified fibrinogen for these samples was 33.6, 25.4, and 24.3 for the coronary disease patients samples (curves 1-3 in FIG. 2A) and 35.7 and 35.1 (curves 4 and 5, respectively) for the control plasma. However, the nitrotyrosine content in these samples (expressed as µmol of 3-nitrotyrosine/mol tyrosine) varied: 67, 38.4, and 52 for the coronary artery disease patients and 25.2 and 25.4, for the controls, respectively.

To investigate the potential effect of fibrinogen nitration on turbidity changes and other properties of the protein, nitrated and oxidized fibrinogens were prepared by chemical treatments described in detail under "Materials and Methods" hereinabove. The yield of nitration after exposure to either 60 nM MPO plus 100 µM $H_2O_2$ and 100 µM $NO_2^-$ or 100 µM SIN-1, was 65±8 and 46±4 µmol 3-nitrotyrosine/mol tyrosine (n=3-5), respectively, as assessed by liquid chromatography/electrospray ionization/tandem mass spectrometry (Shishehbor et al. (2003) J. Am. Med. Assoc., 289:1675-1680; Brennan et al. (2002) J. Biol. Chem., 277:17415-17427). These values were in close proximity to more than half of the coronary disease patient values that exceeded the mean value of 38±14 µmol of 3-nitrotyrosine/mol tyrosine. Data in FIG. 2B reveal that the polymerization of fibrin catalyzed by thrombin monitored by changes in turbidity at 350 nm show a rapid rise in the sample of fibrinogen treated with $MPO/H_2O_2/NO_2^-$ as compared with the protein oxidized by MPO and $H_2O_2$. The same increase in turbidity was also observed with fibrinogen exposed to nitration conditions using SIN-1 in the presence of $CO_2$ as compared with control or fibrinogen exposed to SIN-1 in the presence of superoxide dismutase (FIG. 2C). In these experiments similar to the observations in coronary artery disease plasma, the lag phase in fibrin polymerization decreased, the maximum rate of turbidity for the first 500 seconds after the lag phase increased (Table I), and the final turbidity was greater than in the control curves, suggesting alterations of clot structure.

TABLE I

| Treatment of Fibringogen | $V_o(s^{-1}) \times 10^{-4}$ | Nitrotyrosine (µmol)/mol tyrosine | mol of carbonyl/mol of fibrinogen |
|---|---|---|---|
| $MPO + H_2O_2/NO_2^-$ | 23.3 ± 1.9[a] | 65 ± 8 | 0.71 ± 0.36[a] |
| $MPO + H_2O_2$ | 0.42 ± 0.10[a] | ND | 1.54 ± 0.45[a] |
| 100 µM SIN-1 | 10.9 ± 1.0[a] | 46 ± 4 | 0.47 ± 0.07 |
| 100 µM + SOD | 1.19 ± 0.59 | ND | 0.50 ± 0.1 |
| Control | 1.03 ± 0.42 | ND | 0.44 ± 0.08 |

The rate of clot formation ($V_0$) starting 500 seconds after the initiation of the reaction by the addition of thrombin was measured by turbidity changes at 350 nm (n=3-5). Following the different exposures, the nitration of fibrinogen was measured by liquid chromatography/electrospray ionization/mass spectrometry analysis, whereas oxidation was assessed by the formation of carbonyls as described previously (Veklich et al. (1998) Blood, 92:4721-4729). ND, not detected; SOD, superoxide dismutase. [a]p<0.05 after ANOVA using Tukey's post hoc test.

Figure 2:
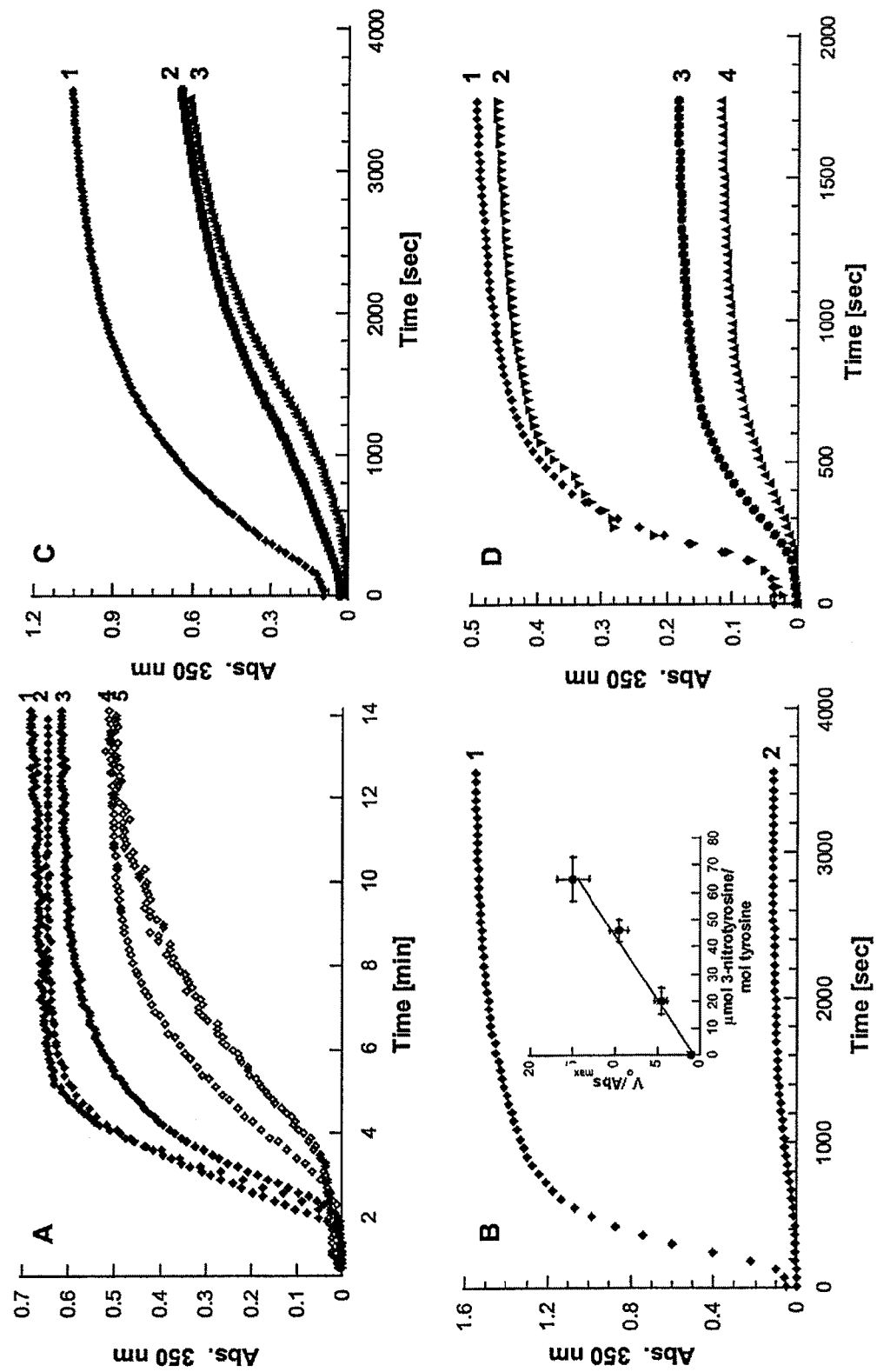
FIGS. 2A-2D are graphs depicting the turbidity changes of plasma samples.

Moreover, the maximum rate of turbidity for the first 500 seconds after the lag phase corrected for the final turbidity increased as a function of the magnitude of fibrinogen nitration (inset, FIG. 2B). The increase in the maximum rate of turbidity of fibrinogen exposed to nitration conditions was sustained even in the presence of oxidized fibrinogen. Fibrinogen that was exposed first to SIN-1 and further oxidized by addition of 100 µM HOCl or fibrinogen that was exposed first to 100 µM HOCl and then to SIN-1 showed the same increase in maximum rate of turbidity as fibrinogen exposed only to SIN-1 (FIG. 2). In contrast fibrinogen exposed to either MPO plus $H_2O_2$ or nitric oxide plus $H_2O_2$ or reagent HOCl failed to show increases in the maximum rate of turbidity (FIG. 2). Extensive oxidation of fibrinogen by the addition of more than 100 µM HOCl results in extensive protein cross-linking and renders the fibrinogen incapable of forming clots.

Figure 3:
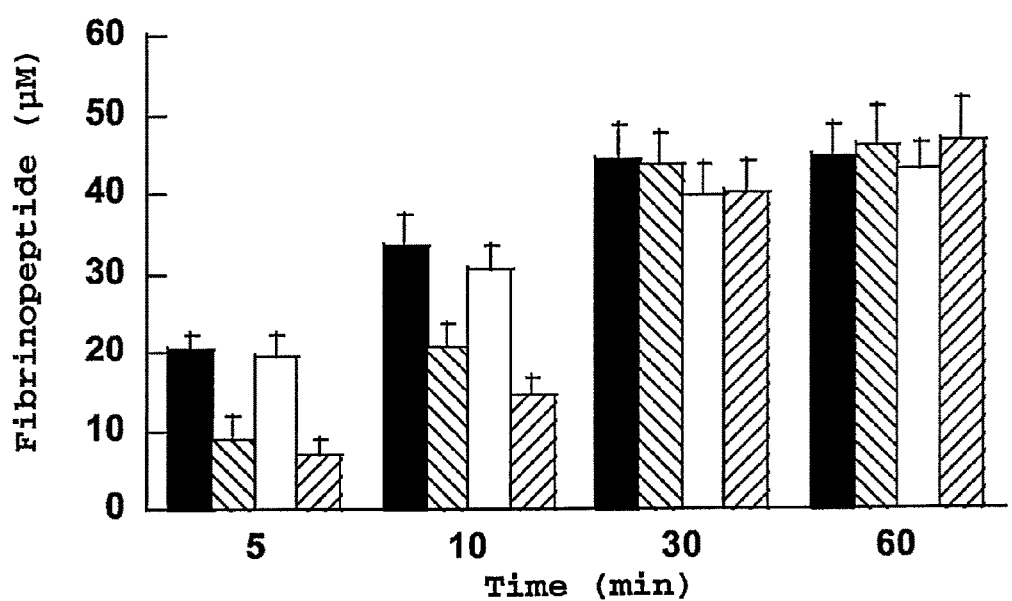
FIG. 3 is a graph demonstrating thrombin-induced fibrinopeptide release. The filled bars represent the release of fibrinopeptide A from a control; the left-hatched bars represent fibrinogen exposed to 60 nM MPO plus 100 μM $H_2O_2$ and 100 μM $NO_2^-$; the open bars represent fibrinopeptide B from a control; and the right-hatched bars represent 60 nM MPO plus 100 μM $H_2O_2$ and 100 μM $NO_2^-$ exposed fibrinogen. Data denote the means±standard deviation (S.D.) of three independent determinations.

The significant increase in the maximum rate of turbidity was not due to acceleration in thrombin cleavage, since quantification of fibrinopeptide A and fibrinopeptide B released by thrombin proteolysis was the same between control and nitrated fibrinogen (FIG. 3).

Factor XIII Cross-linking—Fibrinogen cross-linking factor XIII cross-links both fibrinogen and fibrin. Fibrinogen cross-linking by factor XIII is not different between control and nitrated fibrinogen. However, factor XIII cross-linking of fibrin was accelerated in the nitrated fibrinogen than in control as evident by the disappearance of the Aα and γ chains of fibrinogen (FIG. 4).

Figure 5:
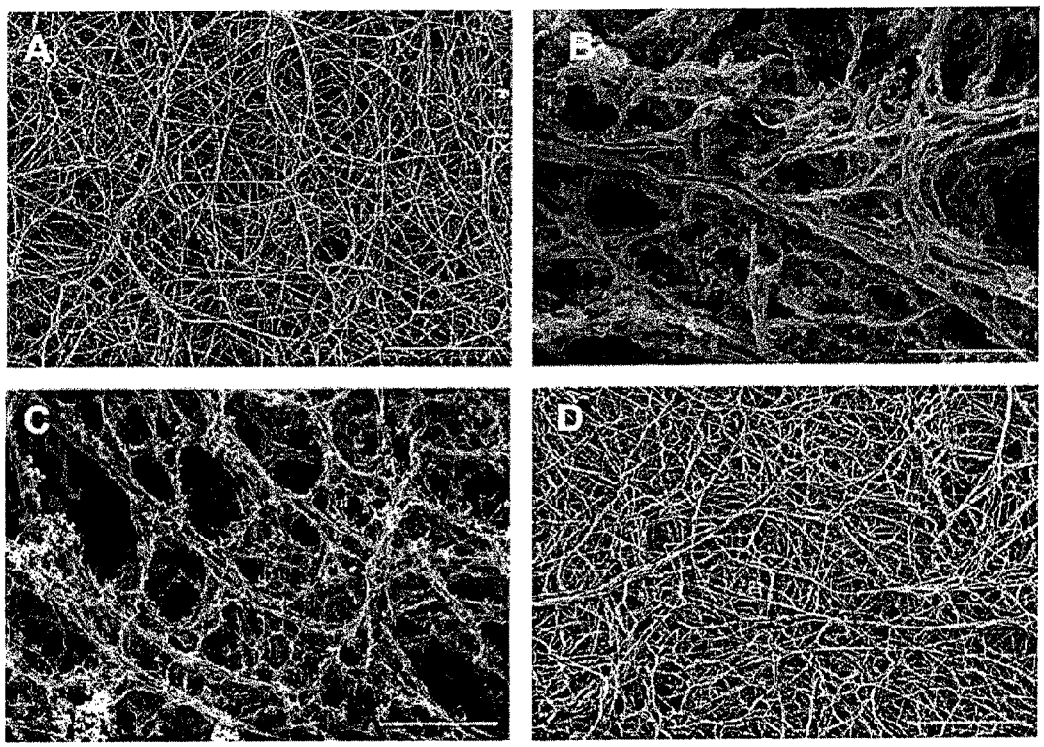
FIGS. 5A-5D are representative scanning electron microscope images of the fibrin clots made from control fibrinogen (FIG. 5A), fibrinogen exposed to 60 nM MPO plus 100 μM $H_2O_2$ and 100 μM $NO_2^-$ (FIG. 5B), fibrinogen exposed to 100 μM SIN-1 (FIG. 5C), and fibrinogen exposed to 60 nM MPO plus 100 μM $H_2O_2$ (FIG. 5D). The scale bar is 10 μm.

Effect of Nitration on Fibrin Clot Architecture, Permeation, and Viscoelastic Properties—The architecture of the fibrin clots formed by control, nitrated, and oxidized fibrinogens was examined by scanning electron microscopy as described previously (Weisel and Nagaswami (1992) Biophys. J., 63:111-128). Fibrin clots formed by fibrinogens exposed to nitrating agents are strikingly different from control or oxidized fibrinogens under identical experimental conditions (FIG. 5). The clots made from fibrinogens exposed to either $MPO/H_2O_2/NO_2^-$ or SIN-1 are made up of thinner fibers, even though the higher turbidity suggested that the fibers would be thicker. However, the fibrin clot made by nitrated fibrinogens is composed of large bundles of the thin fibrin fibers, which scatter light like thick fibers, accounting for the greater turbidity. Higher magnification images also reveal the existence of twisted fibers in nitrated fibrin. A number of large pores are evident in fibrin clots made of nitrated fibrinogens in contrast to the more dense and uniform fibrin network of the oxidized fibrinogen (FIG. 5).

These changes in the architecture of the fibrin clots would be expected to have certain consequences on the physical properties of the clot. Therefore, quantitative changes in the permeation coefficient or Darcy constant were determined by flow measurements made under a constant pressure applied and accounting for geometric parameters of the clot (Ryan et al. (1999) Biophys. J., 77:2813-2826). The permeation coefficient of clots made from fibrinogens exposed to either $MPO/H_2O_2/NO_2^-$ or SIN-1 was significantly higher than the control (Table II). This increase in permeation is accounted for by the presence of large pores, as seen by scanning electron microscopy. A decrease in the Darcy constant was noted in the fibrin clots made of oxidized fibrinogens (Table II), since the pore size in these clots was decreased as compared with control.

TABLE II

| | Darcy constant $K_s$ $cm^2 \times 10^{-10}$ | G' | G" | tanδ |
|---|---|---|---|---|
| Control | 7.5 ± 2.2 | 143.7 ± 38 | 10.5 ± 1.9 | 0.074 ± 0.01 |
| SIN-1 | 584 ± 70$^a$ | 42.7 ± 11$^a$ | 9.1 ± 4.4 | 0.205 ± 0.07$^a$ |
| MPO/ $H_2O_2$ $NO_2^-$ | 1459 ± 259$^a$ | 45.3 ± 9.8$^a$ | 6.2 ± 2.3 | 0.136 ± 0.03$^a$ |
| MPO/ $H_2O_2$ | 0.9 ± 0.4$^a$ | 36.5 ± 5.3$^a$ | 5.0 ± 1.4$^a$ | 0.134 ± 0.03$^a$ |

Exposure of fibrinogen to nitration conditions significantly increased, whereas oxidation significantly decreased, the permeation of clots as compared with control reflected by the changes in the Darcy constant. The Darcy constant was determined in three clots for each condition at two different pressures on 2 different days. Exposure to nitration and oxidation conditions decreased the storage modulus G' forming clots that were less stiff than control clots. The viscoelastic properties of each clot were evaluated in triplicate on three separate clots for each condition on 2 different days. $^a$p<0.05 after analysis of variance using Tukey's post hoc test.

Clot rigidity was then evaluated by measurement of the viscoelastic properties of the fibrin clots made from nitrated or oxidized fibrinogen. Both fibrinogens exposed to nitrating and oxidized conditions produced clots that were considerably less stiff than control reflected by the decrease in storage modulus G' value that is directly related to the stiffness of the clot (Table II). There were no apparent changes in the loss modulus G" or inelastic deformation, but the ratio of inelastic to elastic deformation (tan) was considerably greater for clots made from both fibrinogens exposed to nitrating and oxidizing conditions (Table II).

Figure 6A:
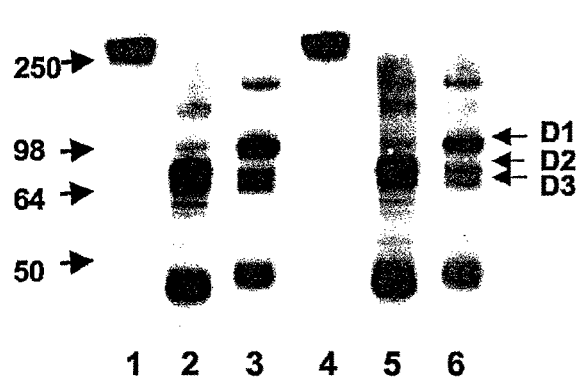
FIG. 6A is a Western blot of control and exposed fibrinogen (lanes 1 and 4) incubated with plasmin (lanes 2, 3, 5, and 6) in the presence of EDTA (lanes 2 and 5) or $CaCl_2$ (lanes 3 and 6); separated on a 7% SDS-PAGE; and detected with an anti-fibrinogen antibody.
Figure 6B:
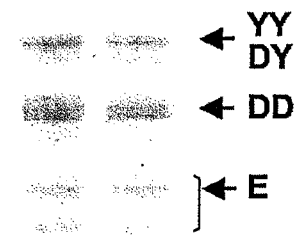
FIG. 6B is a gel representing a control (lane 1) and fibrin clots made from fibrinogen exposed to 60 nM MPO plus 100 μM $H_2O_2$ and 100 μM $NO_2^-$ (lane 2) digested for 1 hour, separated on a 4-12% gradient gel, and stained with colloidal blue.
Figure 6C:
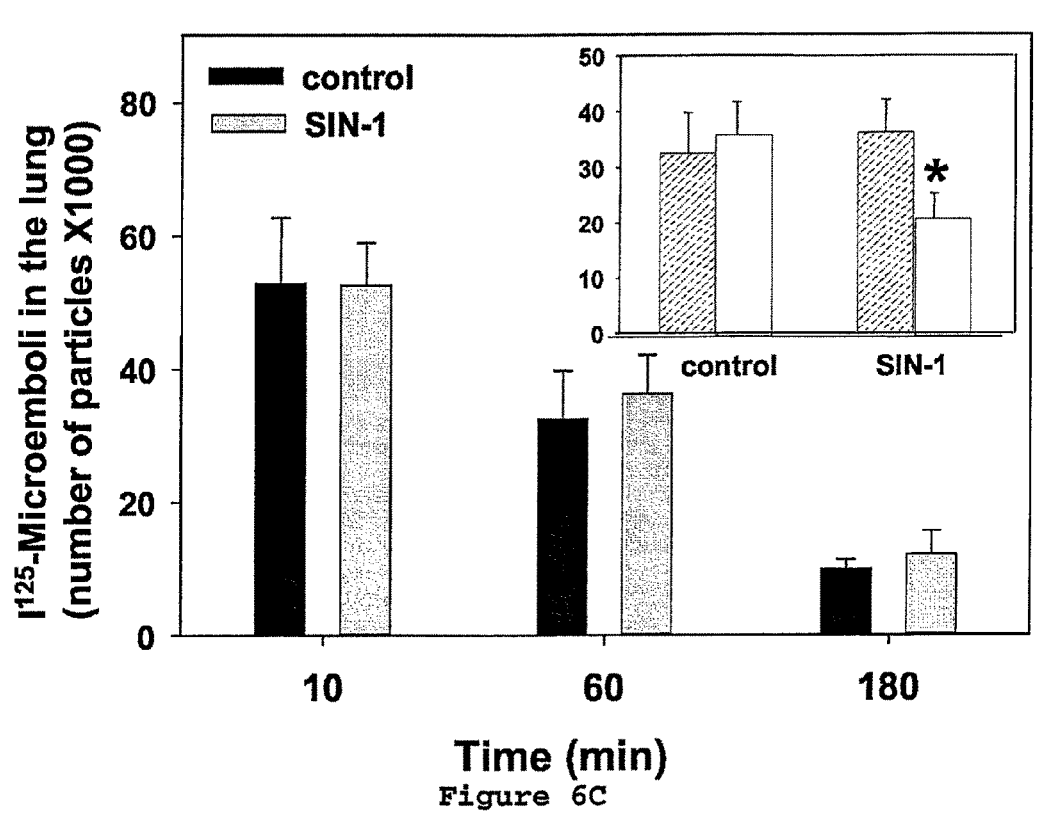
FIG. 6C is a graph of the kinetics of microemboli dissolution in mice following injection of $^{125}$I-fibrin microparticles. The inset is a graph depicting the dissolution of microparticles after administration of tPA (values indicate the number of particles in the lung at initiation and 60 minutes after addition of tPA (white bars) or saline (hatched bars)). Values represent mean±S.D. of n=3-5 independent determinations.

Plasmin Protection Assay and Clot Lysis—Incubation of fibrinogen with plasmin in the presence of EDTA results in the digestion of fibrinogen to D1, D2, D3, and E fibrinogen fragments (Veklich et al. (1998) Blood, 92:4721-4729; Collet et al. (2000) Arterioscler. Thromb. Vasc. Biol., 20:1354-1361). No difference in the plasmin-induced fragmentation between control and fibrinogen exposed to nitrating conditions was observed (FIG. 6A). Incubation of fibrinogen with 5 mM $CaCl_2$ retards equally the plasmin-induced digestion in both the control and nitrated fibrinogen. Moreover, plasmin digestions of fibrin clots made from control or fibrin made from fibrinogen exposed to nitrating conditions were cleaved to the same products yielding the predicted YY, DY, DD, and E fragments (FIG. 6B). The lysis rate between the control and fibrin clots made from fibrinogen exposed to nitrating conditions in vitro was the same after normalizing the data to the same starting turbidity and expressing it as percent lysis over time. The value for control clots was $0.10 \pm 0.03 \times 10^{-2}$ s$^{-1}$ (n=5) and $0.12 \pm 0.02 \times 10^{-2}$ s$^{-1}$ (n=5) for clots made from fibrinogen exposed to nitrating agents, suggesting that the alterations in the physical properties of the fibrin clots induced by nitration do not significantly impact the proteolytic cleavage of the clots. The in vitro data were further validated in vivo by measuring the rate of clearance of microemboli made from control and nitrated fibrinogens after injection of radiolabeled microemboli ($^{125}$I-ME) with a mean diameter 2-5 μm in the tail vein of anesthetized mice (FIG. 6). As described previously, $^{125}$I-ME rapidly lodge in the pulmonary vasculature after intravenous injection in mice and rats alike and, nearly 30 minutes after pulmonary deposition, undergo spontaneous dissolution that is completed within 5 hours (Veklich et al. (1998) Blood, 92:4721-4729; Collet et al. (2000) Arterioscler. Thromb. Vasc. Biol., 20:1354-1361). Experiments in mice with genetically altered background revealed that both endogenous tissue type and urokinase plasminogen activator contribute to spontaneous dissolution of $^{125}$I-ME lodged in the pulmonary vessels. Injection of exogenous plasminogen activators (e.g. activase and tPA) markedly accelerates dissolution of $^{125}$I-ME deposited in rat and murine lungs and compensates for genetic ablation of the corresponding plasminogen activator (Murciano et al. (2002) Am. J. Physiol., 282:L529-L539; Bdeir et al. (2000) Blood, 96:1820-1826). There was no significant difference in pulmonary deposition and rate of spontaneous dissolution of $^{125}$I-ME prepared from intact versus nitrated fibrinogen in mice (FIG. 5C). However, $^{125}$I-ME prepared from nitrated fibrinogen displayed markedly higher susceptibility to "therapeutic" fibrinolysis (inset in FIG. 6C). Thus, intravenous injection of a marginally effective dose of tPA (30 μg/kg), which had no effect on the rate of dissolution of normal $^{125}$I-ME, induced a detectable acceleration of dissolution of the nitrated $^{125}$I-ME (p<0.05). These data imply that fibrinogen nitration does not alter susceptibility of blood clots to spontaneous fibrinolysis, yet may be more amiable to fibrinolytic therapy.

Platelet Aggregation and Binding—The effects of control and nitrated fibrinogens upon the rate of human platelet aggregation and platelet binding were examined utilizing protocols established previously (Bennett and Vilaire (1979) J. Clin. Investig., 64:1393-1401). The rate of ADP-induced platelet aggregation was the same for control and fibrinogens exposed to 100 µM SIN-1. Similarly the adherence of platelets to immobilized fibrinogen on multiwell plates was the same for control and nitrated fibrinogens.

Discussion

A number of studies have provided evidence for an association between the pro-thrombotic state and risk for adverse outcomes such as myocardial infarction, sudden death, and stroke in coronary artery disease patients (Wilhelmsen et al. (1984) N. Engl. J. Med., 311:501-505; Kannel et al. (1987) J. Am. Med. Assoc., 258:1183-1186; Thompson et al. (1995) N. Engl. J. Med., 332:635-641; Salomaa et al. (1995) Circulation, 91:284-290). The present invention provides a biochemical link between thrombosis and inflammation by showing both increased levels of nitrated fibrinogen in coronary artery disease subjects and functional alterations in fibrinogen/fibrin consistent with generation of a pro-thrombotic state. The instant invention indicates a link between enhanced nitrative stress and potential for pro-thrombotic state in patients with coronary artery disease.

Previous studies (Gole et al. (2000) Am. J. Physiol., 278: L961-L967; Pignatelli et al. (2001) Cancer Res., 61:778-784) have identified nitrated fibrinogen in patients with clinically documented acute respiratory distress syndrome (ARDS) and lung cancer. Fibrin deposits are abundant in the lungs of patients with ARDS, a common complication of hemorrhagic injury and sepsis, and are likely the result of abnormal clotting rather than failure in the fibrinolytic pathways, which apparently function normally in ARDS patients (Gole et al. (2000) Am. J. Physiol., 278:L961-L967). The findings in the human ARDS are in part confirmed by proteomic identification of nitrated fibrinogen in the lungs of rats exposed to lipopolysaccharide (Aulak et al. (2001) Proc. Natl. Acad. Sci. U.S.A., 98:12056-12061). The data presented here in coronary artery disease patients and previously in ARDS and cancer patients indicate that fibrinogen is a target for modification by reactive nitrogen species in vivo, consistent with the potential contribution of these processes in the pathogenesis of atherosclerosis and acute lung injury.

Observed changes in fibrinogen properties may not be exclusively limited to tyrosine nitration because nitration of proteins quite often occurs in conjunction with oxidation of other amino acid residues. For example, fibrinogen immunoprecipitated from the plasma of cancer patients demonstrated increased content of carbonyl adducts, suggesting that fibrinogen was either oxidized or modified by the addition of aldehydic oxidized lipid species (Pignatelli et al. (2001) Cancer Res., 61:778-784). Indeed, oxidation of fibrinogen by $MPO+H_2O_2$ or HOCl resulted in the formation of 1.54 mol of carbonyl adduct per mol of protein and induced a decrease in the rate of fibrin polymerization producing fibrin clots with decreased permeation properties. This is consistent with previous findings that indicated that formation of 1.8 mol of carbonyl adduct per mol of protein in fibrinogen (Shacter et al. (1995) Free Radic. Biol. Med., 18:815-821) or oxidation of histidine, tryptophan, and methionine residues resulted in the inhibition of thrombin-induced polymerization of fibrinogen despite a normal rate of fibrinopeptide release (Inada et al. (1978) Biochim. Biophys. Acta, 532:161-170; Stief et al. (1991) Thromb. Res., 61:191-200; Belisario et al. (1997) Biochimie (Paris), 79:449-455; Lupidi et al. (1999) FEBS Lett., 462:236-240). In contrast, exposure of fibrinogen to nitrating conditions such as $MPO/H_2O_2/NO_2^-$, which resulted in both oxidation and nitration of the protein (Table I), resulted in a significant increase in the maximum turbidity, generating fibrin clots with distinct architecture and increased permeation as compared with oxidized fibrinogen (FIG. 5). It is interesting to note that changes in the properties of fibrinogen and fibrin clots observed after treatment of the protein with nitrating agents occurred in the absence of dityrosine cross-linking and without alterations in the secondary structure of fibrinogen, as assessed by CD spectroscopy. Fibrinogen exposed to nitrating agents was able to maintain the ability to aggregate and adhere to platelets. These findings are consistent with a previous report showing that oxidation of tyrosine residues to form dityrosine, as well as conformational changes detected by 8-anilino-1 naphthalenesulfonic acid binding in fibrinogen, resulted in a significant decline in platelet adhesion and ADP-stimulated platelet aggregation (Belisario et al. (1997) Biochimie (Paris), 79:449-455). Taken together the dramatically opposing effect of nitrating compared with non-nitrating oxidants strongly indicates that nitration of fibrinogen tyrosyl residues is responsible for the alterations observed in selective fibrinogen/fibrin properties and functions.

The decrease in the lag period of turbidity measurements in nitrated fibrinogen (FIG. 2) indicates an increase in the rate of small oligomer formation, whereas the dramatic increase in the maximal rate of turbidity indicates a significant augmentation in the rate of lateral aggregation. Furthermore, the nature of the effects on clot structure, particularly the presence of many fiber ends and large pores in the clots, suggests that nitrated molecules may "cap" the ends of growing protofibrils, preventing or retarding further growth. Kinetic modeling studies of changes in the rate constants resulting from capping that have been carried out are consistent with the observed effects on the polymerization curves (Weisel and Nagaswami (1992) Biophys. J., 63:111-128). In addition, such effects could be present with only a few modified molecules as is the case with nitrated fibrinogen.

The viscoelastic properties of fibrin clots have been associated with complications of coronary heart disease (Scrutton et al. (1994) Blood Coagul. Fibrinolysis, 5:719-723; Peltonen et al. (1993) Arterioscler. Thromb., 13:1738-1742; Fatah et al. (1992) Thromb. Haemostasis, 68:130-135; Fatah et al. (1996) Thromb. Haemostasis, 76:535-540). Higher fibrinogen levels have been associated with formation of a less deformable fibrin clot (clot with increased stiffness), which is more likely to occlude blood flow than a more deformable clot (Scrutton et al. (1994) Blood Coagul. Fibrinolysis, 5:719-723). The two above-cited studies by Fatah et al. described the in vitro formation of fibrin gels, made from patient plasma with documented heart disease, with abnormal gel network characterized by less porous and resilient and more space-filling structures. The biochemical reasons for the formation of these abnormal fibrin gels is not known but was not related to fibrinogen concentration and was postulated to result from post-translational modifications such as deglycosylation or other unidentified alterations of fibrinogen (Langer et al. (1988) J. Biol. Chem., 262:15056-15063). The architecture of these fibrin gels is different from the clots obtained from nitrated fibrinogen. The subjects of the aforementioned studies had experienced adverse effects such as myocardial ischemia before the age of 45, and it is possible that in these individuals the majority of the nitrated fibrinogen has been deposited in the lesions (Smith et al. (1990) Arteriosclerosis, 10:263-275; Bini et al. (1987) Blood, 69:1038-1045). Moreover, the viscoelastic properties of fibrin made from fibrinogen exposed to nitration conditions are consistent with the observations of clot structure determined by scanning electron microscopy. Fibrin clots made from nitrated fibrinogen are formed primarily of thin fibers that give rise to high turbidity because of their bundling into groups. The decrease in the storage modulus (G') or stiffness of the clots made from nitrated fibrinogen is consistent with the observed structure, since these clots are composed of thinner fibers with many free fiber ends. Clots made up of thin fibers that have many branch points are generally stiffer than clots with thicker fibers and fewer branch points. However, clots with bundled thin fibers with many free ends would behave more like clots with very thick fibers. The free fiber ends allow fibers to move past each other, giving rise to an increase in the tan or ratio of non-elastic to elastic components. The mechanical properties of these clots suggest a connection to pathological conditions. The weaker clots made from nitrated fibrinogen may fragment more easily upon mechanical stresses and thus increase the potential risk for microemboli formation. These observations are similar to reported effects of tyrosine acetylation (Philips and York (1973) Biochemistry, 12:3642-3647). Acetylation of two tyrosine residues in fibrinogen produced a fibrin clot with a 50% reduction in clot strength (Philips and York (1973) Biochemistry, 12:3642-3647).

Collectively, the present data indicates that tyrosine nitration selectively alters fibrinogen function, promotes clot acceleration and induces specific alterations in clot structure, and viscoelastic properties. The increased rate of polymerization, leading to an imbalance in the dynamic equilibrium between clotting and lysis and the risk of clot fragmentation, indicates an association between nitration of fibrinogen and the incidence of adverse effects in coronary artery disease.

EXAMPLE II

The quantification of nitrated fibrinogen was performed by purification of fibrinogen from patient plasma using affinity chromatography in which the Fc portion of a monoclonal anti-fibrinogen antibody was coupled to protein A. The ability of the anti-fibrinogen column to capture nitrated fibrinogen was confirmed by using in vitro nitrated fibrinogen. The eluted fibrinogen was then hydrolyzed in order to quantify the protein 3-nitrotyrosine levels by HPLC with on-line electrospray ionization tandem mass spectrometry using stable isotope dilution methodology and an ion trap mass spectrometer (LC/ESI/MS/MS). The values were normalized to the levels of tyrosine to avoid changes in fibrinogen levels among patients. A 30% increase (p<0.001) in the levels of nitrated fibrinogen was found in coronary artery disease patients (n=30) as compared to age-matched controls (n=26).

However, this method is not the most suitable for large population studies entailing a high throughput quantification of fibrinogen and nitrated fibrinogen. Therefore, as enzyme-linked immunosorbent assay (ELISA) was developed for the quantification of fibrinogen and a separate ELISA for the quantification of nitrated fibrinogen.

Figure 7:
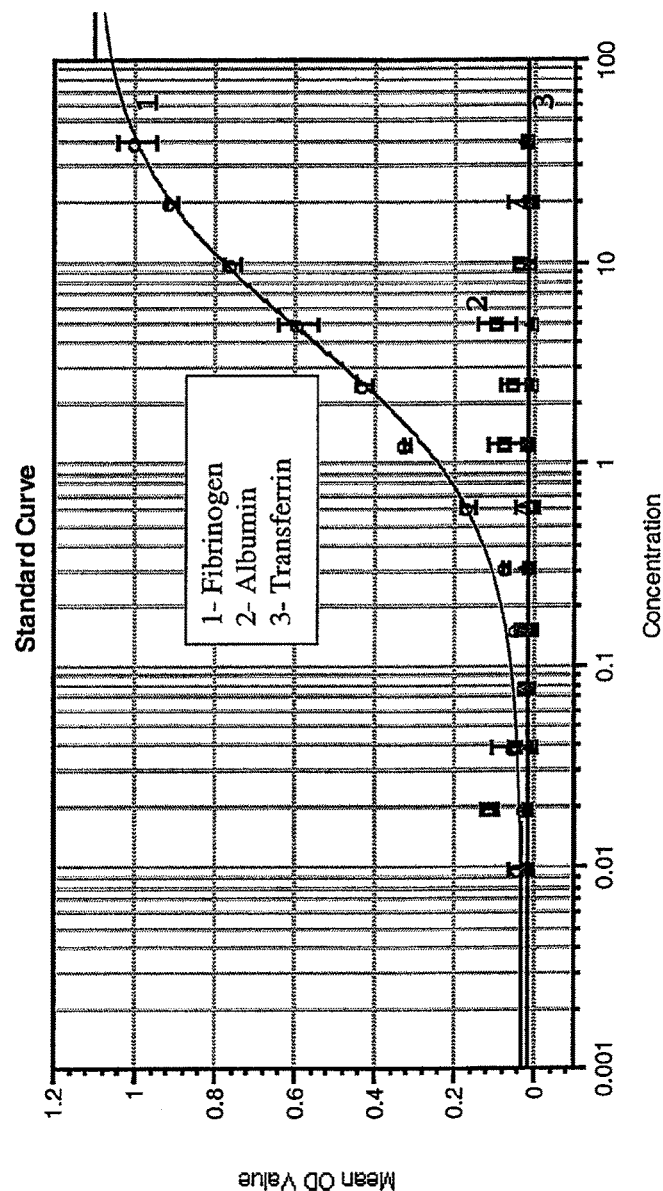
FIG. 7 is a graph depicting the standard curve for fibrinogen quantification by a sandwich ELISA.

For these ELISA assays, monoclonal antibodies were raised against fibrinogen in mice. Two out of 3 clones with high affinity and avidity were selected and used in a sandwich ELISA to quantify fibrinogen levels in human plasma. FIG. 7 depicts a typical standard curve using purified fibrinogen. Specifically, monoclonal anti-fibrinogen antibody (clone 23C4A) was coated overnight at 4° C. on 96 well plates. After blocking and washing, plasma was added at different dilutions and allowed to incubate for 2 hours at 37° C. In a triplicate set, purified fibrinogen was added in the range of 1-500 ng/mL to generate a standard curve (FIG. 7). A second anti-fibrinogen antibody (clone 3D2A9) that was conjugated with horseradish peroxidase was added for 2 hours at 37° C. The plate was developed using peroxide and 3,3',5,5'-tetramethylbenzidine (TMB) as substrate and the absorbance at 450 nm was recorded. The numbers indicate the mean+/−standard deviation values obtained in control individuals and individuals that smoke cigarettes. These values are well within previously reported values.

Figure 8A:
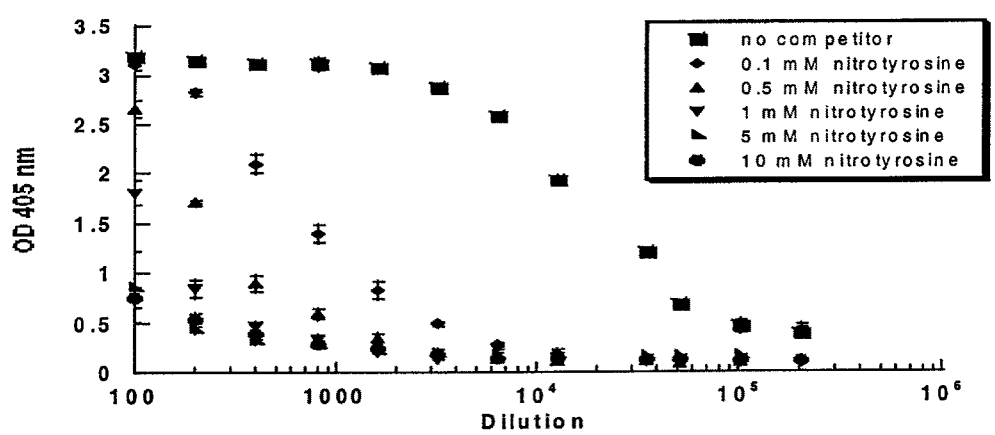
FIG. 8A is a graph depicting the competition of antibody binding to nitrated fibrinogen after the antibody was pre-incubated with different concentration of the free ligand, 3-nitrotyrosine.
Figure 8B:
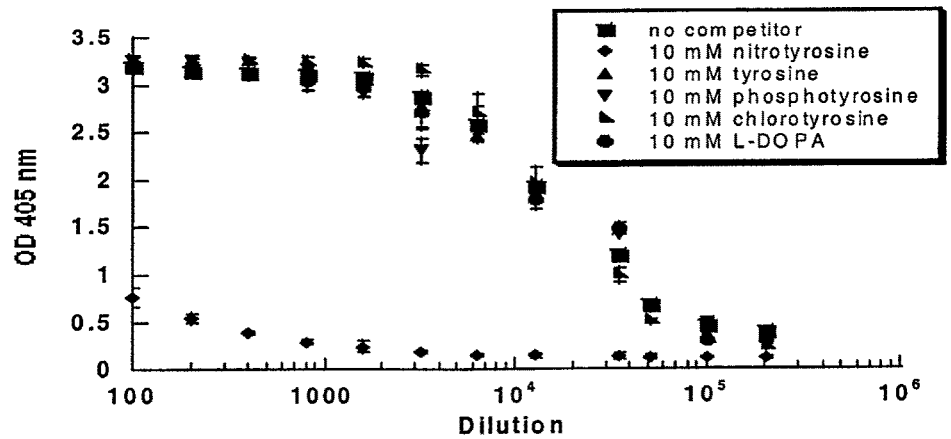
FIG. 8B is a graph depicting the competition of antibody binding to nitrated fibrinogen with tyrosine and various substituted tyrosines. The specified compounds were incubated with the antibody for 3 hours at room temperature in a standard ELISA using nitrated human fibrinogen as the adsorbed antigen. Data points represent the mean±S.D. of 3 microplate wells for each antibody dilution.

To quantify nitrated fibrinogen, the ELISA may be modified such that the capturing antibody is a monoclonal anti-fibrinogen antibody and the second antibody is an affinity purified polyclonal antibody that recognizes nitrated proteins and specifically tyrosine nitrated residues in the β-chain of fibrinogen. The aforementioned polyclonal antibody was raised against a synthetic peptide, the octapeptide (Cys-Gly-NO$_2$Tyr-Gly-Gly-Gly-NO$_2$Tyr-Gly; SEQ ID NO: 1) that includes two nitrotyrosine residues. The antibodies were affinity-purified (using a nitrotyrosine column), and the purity was confirmed by SDS electrophoresis. The competition ELISA depicted in FIGS. 8A and 8B show the specificity of the antibody. The data shows a specific and concentration dependent decline in binding as the concentration of 3-nitrotyrosine increases. No cross-reactivity was found against tyrosine, phosphotyrosine, chlorotyrosine, methyltyrosine and dopamine. Furthermore, pre-adsorption with 3-nitrotyrosine completely abolished the immune reaction, thereby further validating the specificity of the assay. Moreover, the data in Table III show a very good correlation between the ELISA for nitrated fibrinogen versus the affinity capture LC/ESI/MS/MS method.

TABLE III

| Subject | Nitrated fibrinogen by LC/ESI/MS/MS μmol/mol | Nitrated fibrinogen by ELISA μmol/mol |
| --- | --- | --- |
| 1 | 28.5 | 32.0 |
| 2 | 21.5 | 31.0 |
| 3 | 23.3 | 21.2 |
| 4 | 23.7 | 21.7 |
| 5 | 40.0 | 41.0 |
| 6 | 20.0 | 20.2 |

Figure 9:
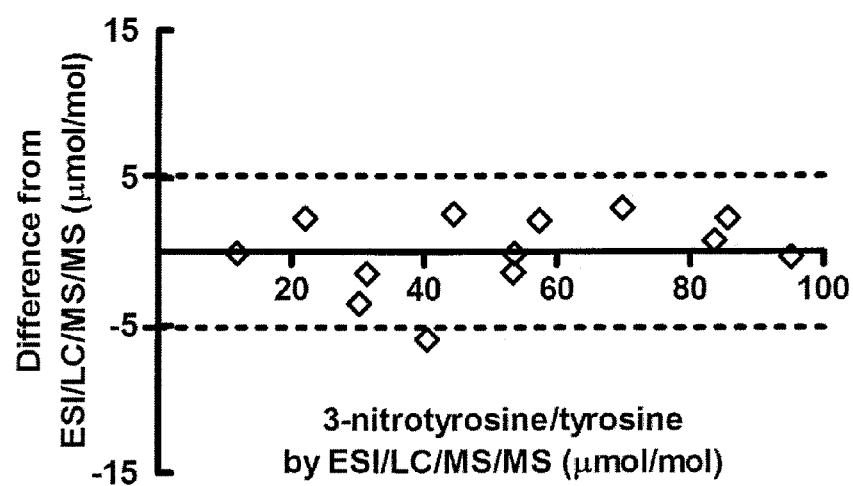
FIG. 9. Bland-Altman plot that compares the nitrotyrosine/tyrosine values from 14 samples obtained by the ELISA assay and by stable isotope dilution LC-MS/SM. The values obtained by the latter method are plotted on x-axis and the average difference in values between the two methods is plotted on the y-axis. The bias is calculated 0.029±2.62 μmol/mol (the average of the differences±SD) and the 95th confidence interval (dotted lines) extended from −5.11 to 5.17 μmol/mol.

The ELISA described above for the quantification of nitrated fibrinogen was found to have a linear range for from 1 to 10 nM. The ELISA has an intra-assay variation of 15% and an inter-assay variation of 14%. The data in FIG. 9 shows the validation of the ELISA by comparing the method to the "gold standard" of LC-MS/MS. A sound agreement between the two methods was obtained, which therefore allows for the rapid and reproducible evaluation of nitrated fibrinogen in plasma samples by ELISA.

The ELISA for total fibrinogen employs a mouse monoclonal anti-human fibrinogen antibody (23C4A9), developed by standard techniques, which recognizes unmodified, nitrated and oxidized forms of fibrinogen. The linear range for this ELISA extends from 0.02-0.625 μg/ml. The precision and reproducibility of this assay was assessed with 10 repetitive analyses of a quality control plasma sample. This ELISA has an intra-assay variation of 10% and an inter-assay variation of 9%. Using these two validated ELISA assays, the levels of fibrinogen and nitrated fibrinogen was quantified in 35 subjects with acute deep venous thrombosis (DVT), as documented by venous duplex ultrasound, and compared with levels in healthy control subjects matched for gender and age as well as against heavy smokers (11-20 cigarettes/day) with a history of 4-20 years of smoking as described above in this application. Subjects with DVT were recruited from the Cleveland Clinic vascular laboratory among patients diagnosed acute DVT on venous duplex ultrasound examination. DVT patients and those at risk for developing DVT and venous thrombosis include patients with thrombosis of the lower extremities and pulmonary embolisms. All subjects with DVT were enrolled prior to the initiation of anticoagulation therapy and plasma was rapidly collected and stored at −80° C.

Figure 10:
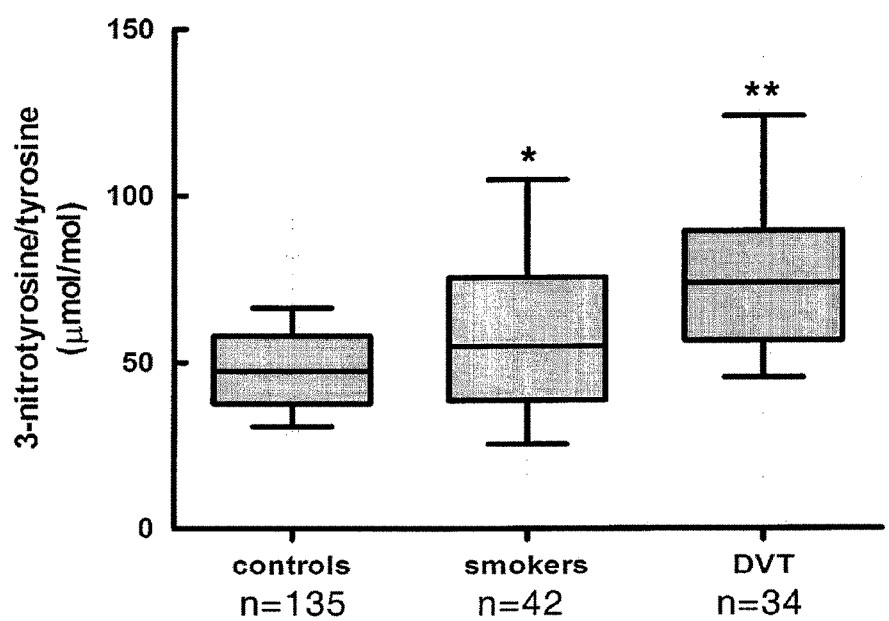
FIG. 10. Box-whisker plots of 3-nitrotyrosine levels in fibrinogen versus DVT status. Boxes encompass the 25th and 75th percentiles and lines within boxes represent median values. Bars represent the 2.5[th] and 97.5[th] percentiles. *p<0.05 compared to controls, **p<0.05 compared to controls and smokers.

The data in FIG. 10 indicate significantly higher levels of nitrated fibrinogen in the DVT subjects as compared to heavy smokers and controls.

EXAMPLE III

As described in this application, a mechanism for an increased pro-thrombotic state is the post-translational modification of fibrinogen by tyrosine nitration. Using affinity capture of fibrinogen followed by stable isotope, liquid chromatography/tandem mass spectrometry (LC/MS/MS) quantification demonstrated increased levels of nitrated fibrinogen in coronary artery disease subjects (8). Furthermore, biochemical and biophysical experiments indicated that nitration of fibrinogen in vitro accelerated the formation, altered the architecture and viscoelastic properties of the fibrin clot (8). These studies have therefore suggested a potentially unrecognized link between enhanced nitrative/oxidative stress and pro-thrombogenic events. In this example, evidence is provided that nitration of fibrinogen in vivo results in changes in the kinetics (i.e., increased initial velocity of fibrin clot formation), architecture (i.e., altered fibrin clot architecture), stiffness of fibrin clots (i.e., increased fibrin clot stiffness) and fibrinolysis (i.e., reduced the rate of clot lysis) consistent with an increased risk for thrombotic complications.

Results

Increased Levels of Fibrinogen Nitration in Smokers

The levels of nitrated fibrinogen were quantified in a population of subjects with no known risk factors for cardiovascular disease other than smoking. Circulating levels of nitrated fibrinogen were significantly elevated in heavy smokers compared to non-smokers (51.0±5.5 vs. 36.0±3.2 μmol 3-nitrotyrosine/mol tyrosine, mean±SEM, p=0.04, n=31).

Beta Chain of Fibrinogen is the Principal Site of Nitration In Vivo

Figure 11:
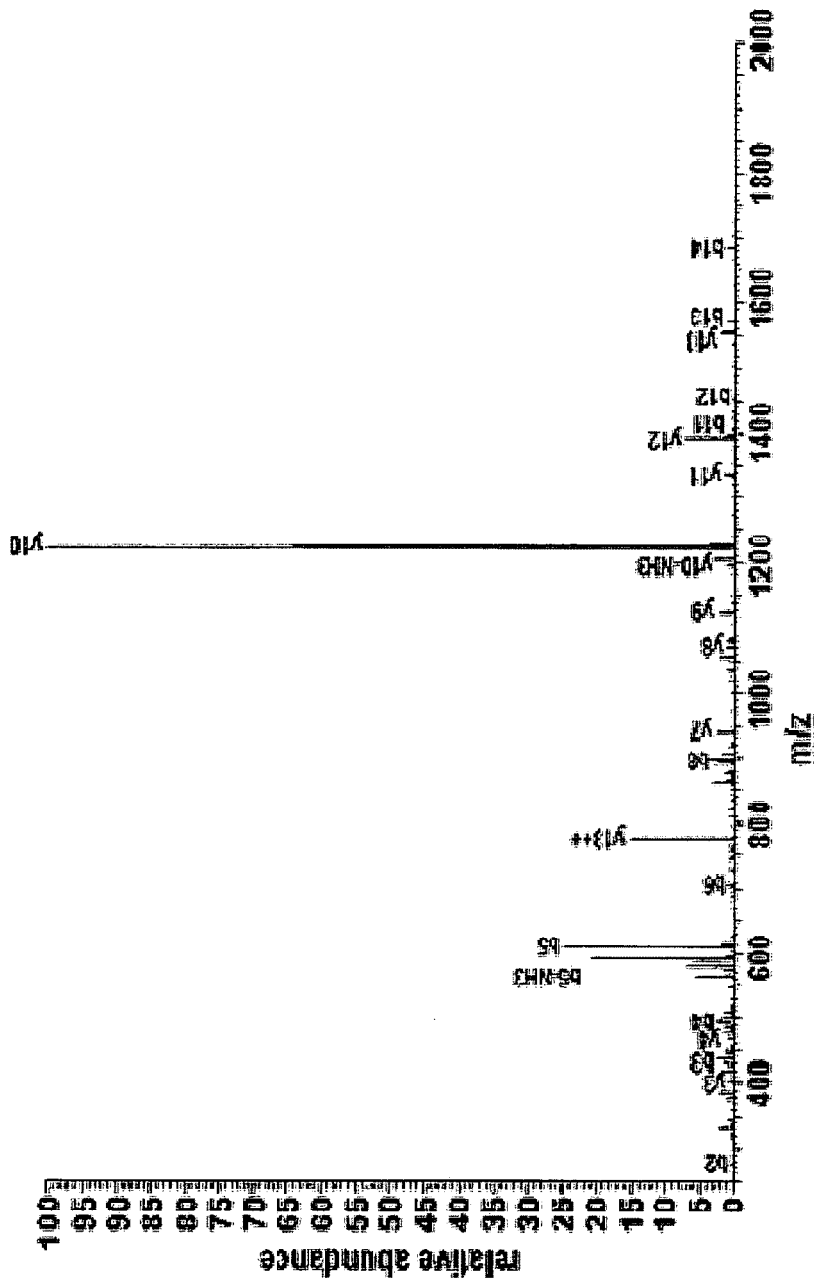
FIG. 11. β-Chain carboxyl terminus tyrosine residues are nitrated in vivo. Panel A: Isolated fibrinogen analyzed on 10% SDS-PAGE gels and stained with colloidal blue. Lane 1: 1 μg/lane of commercial fibrinogen, Lanes 2-7: isolated fibrinogen, 2.5 name with 3-nitrotyrosine/tyrosine ratio <25 μmol/mol (1,2), 25-50 μmol/mol (3,4), >50 μmol/mol (5,6). Panel B: Affinity enrichment for nitrated fibrinogen. Fractions were probed with a polyclonal anti-human fibrinogen antibody (lanes 1-4) or a polyclonal anti-nitrotyrosine antibody (4-7). Lane 1:input fibrinogen, lanes 2&3:washes, lane 4:immunoprecipitated fraction. Panels C&E: Representative MS/MS spectra from the peptides NYCGLPGE[$NO_2$Y]WLGNDK (SEQ ID NO: 2) and YYWGGQ[$NO_2$Y]TWDMAK (SEQ ID NO: 3) respectively. Panel D&F: Representative MS/MS spectra of the peptide NYCGLPGE[$NH_2$Y]WLGNDK (SEQ ID NO: 6) and YYWGGQ[$NH_2$Y]TWDMAK (SEQ ID NO: 7) after reduction.
Figure 11:
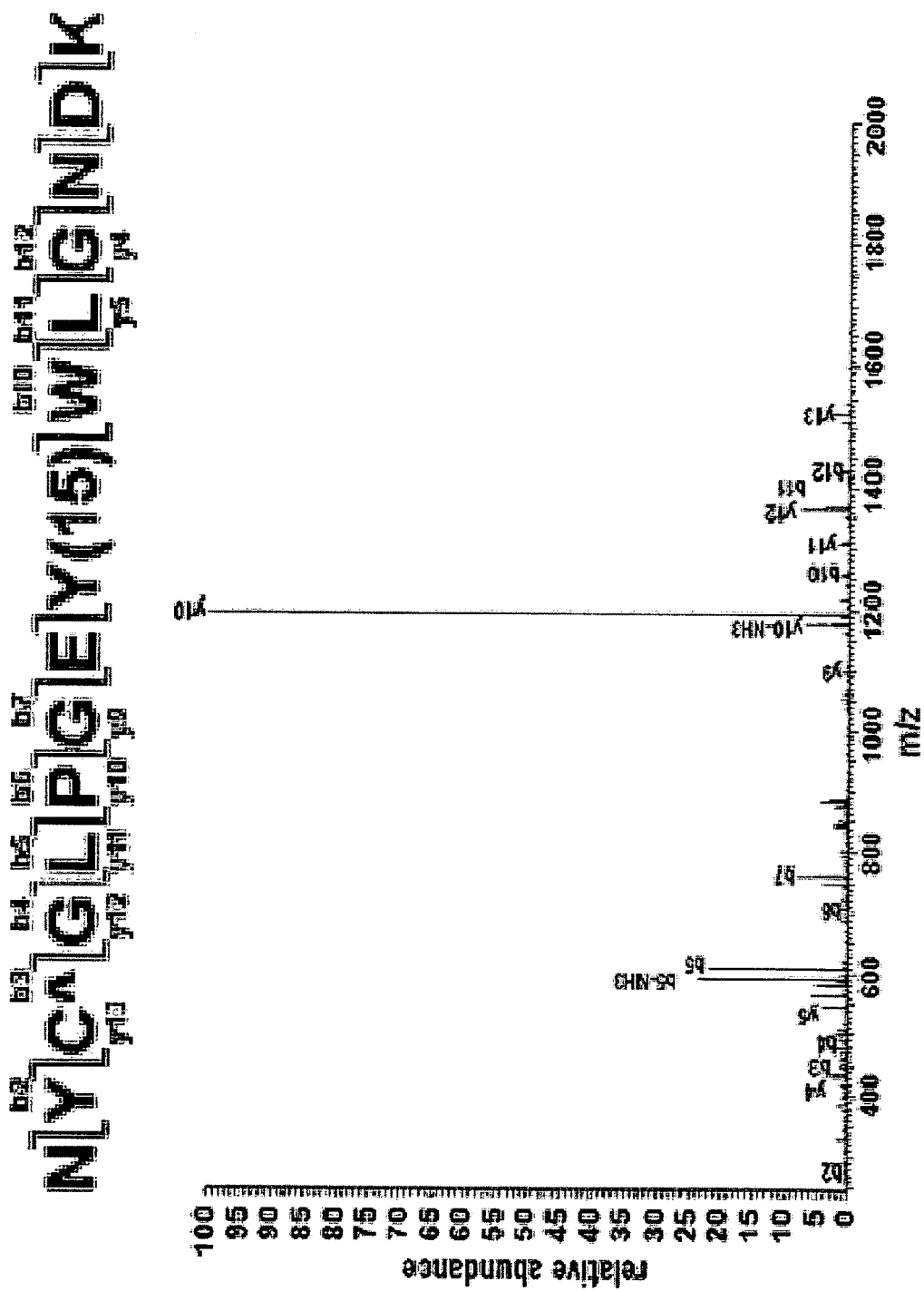
Figure 11:
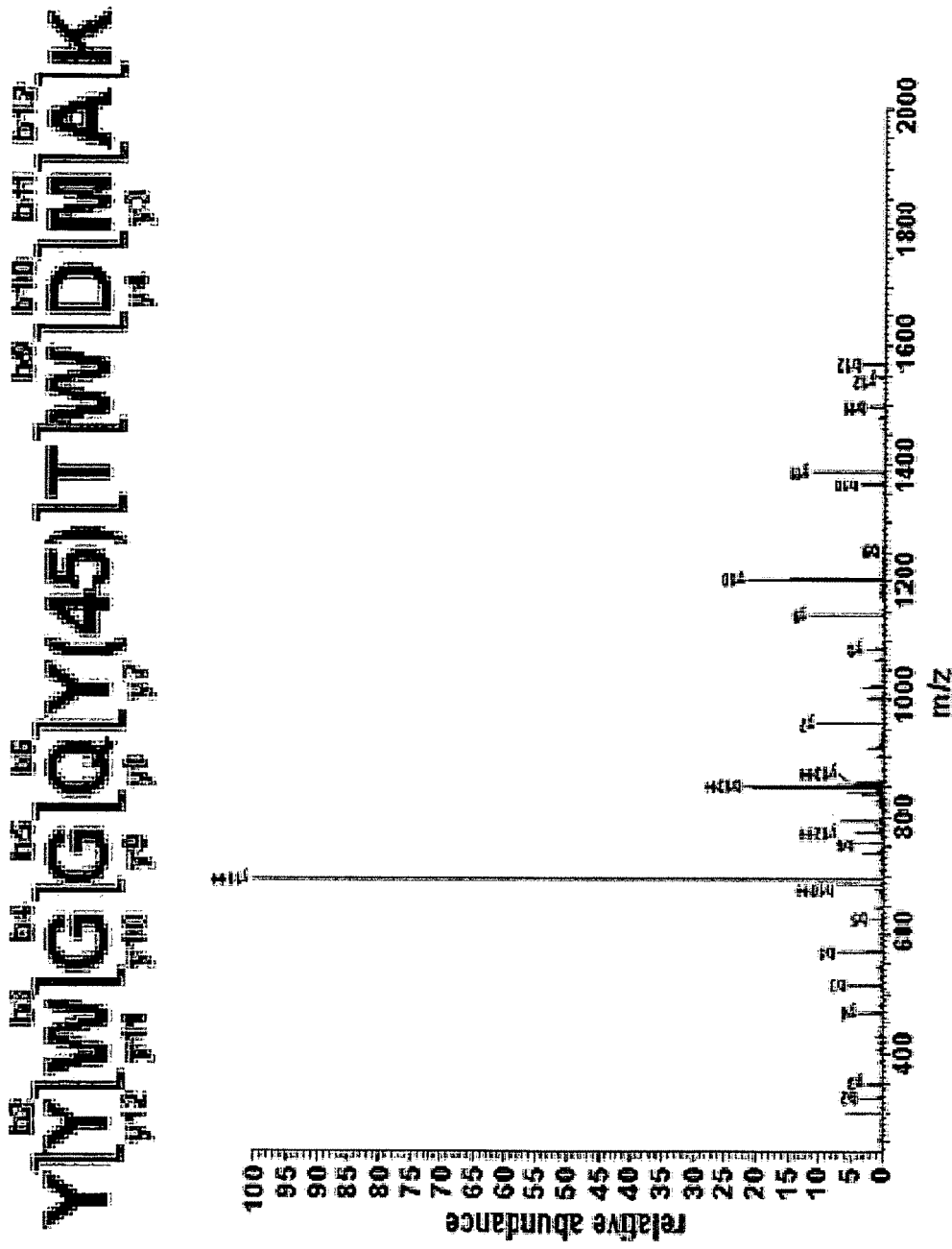
Figure 11:
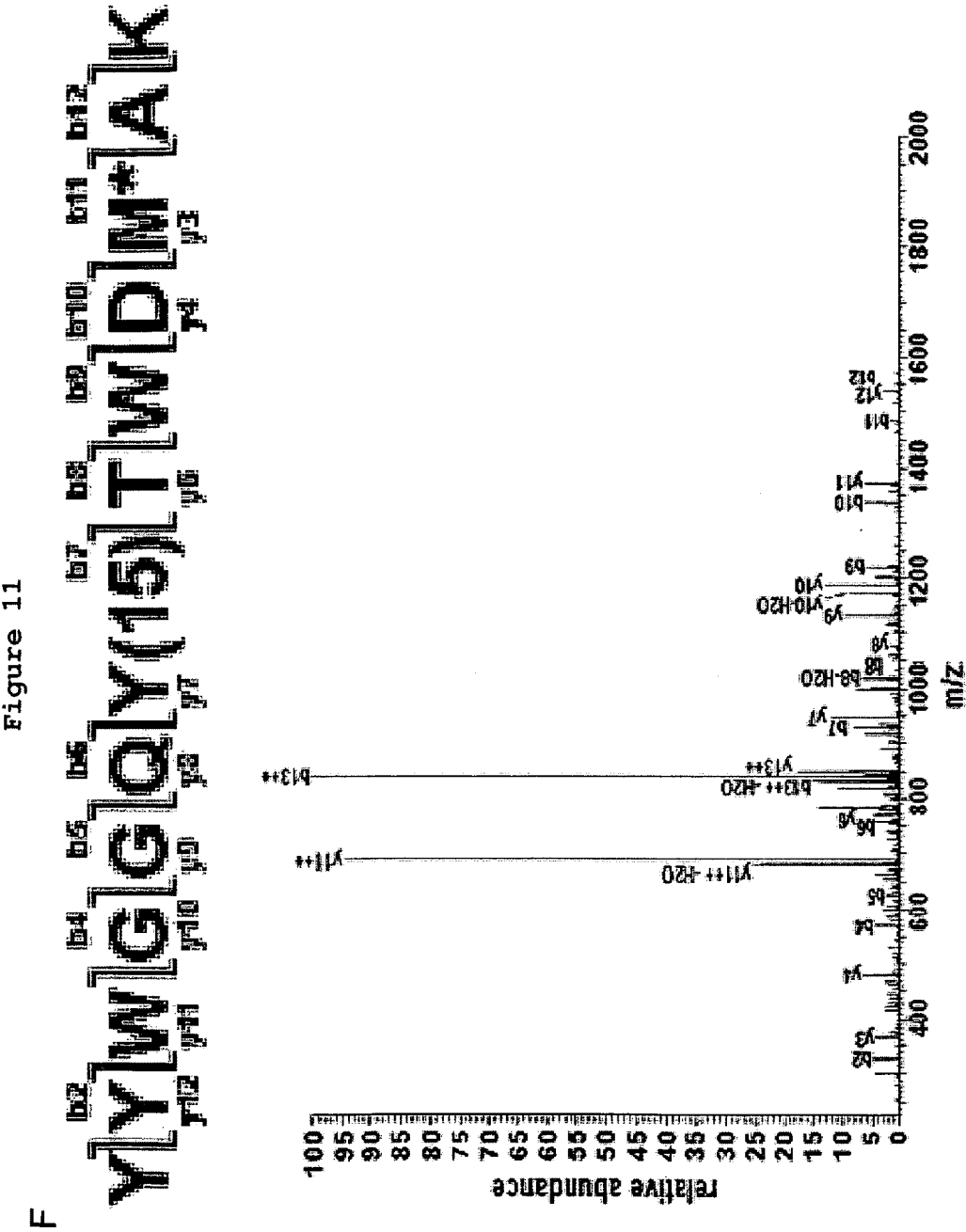

To identify the tyrosine residues targeted by reactive nitrogen species in vivo two complementary approaches to enrich for nitrated fibrinogen or nitrated peptides were employed since a fibrinogen molecule has 134 tyrosine residues. Initially, fibrinogen was isolated from human plasma by glycine precipitation (FIG. 11A). Affinity capturing with anti-nitrotyrosine antibodies was then used to enrich for nitrated fibrinogen molecules. The enriched fractions were analyzed in SDS-PAGE and probed with anti-nitrotyrosine antibodies, which revealed positive reactivity primarily with the β-chain of fibrinogen (FIG. 11B). The enriched fractions were digested with trypsin and analyzed by mass spectrometry. Alternatively, the isolated fibrinogen was first digested with trypsin followed by immunoaffinity enrichment for nitrated peptides. A modified method for peptide capture that employed incubation of peptides with antibodies not linked to agarose beads in 10 kDa cutoff filters was applied in order to reduce non-specific interactions.

Four separate samples were analyzed with the first approach. Each sample consisted of pooled fibrinogen isolated from four individuals. Five putative fibrinogen β-chain tryptic peptides were detected with +45 amu mass increases that mapped to tyrosine residues. The peptide capture approach was then applied to 9 different samples of individual fibrinogen preparations, which were analyzed with an LTQ-Orbitrap hybrid MS instrument. This analysis confirmed with high mass accuracy the presence of two peptides with the expected +45 amu increase. The peptides NYCGLPGE[NO$_2$Y]WLGNDK (SEQ ID NO: 2) and YYWGGQ[NO$_2$Y]TWDMAK (SEQ ID NO: 3) were identified in 6 and 7 out of the 9 samples, respectively. SEQ ID NOs: 2-3 are nitrated and the wild type sequences are NYCGLPGEYWLGNDK (SEQ ID NO: 4) and YYWGGQYTWDMAK (SEQ ID NO: 5). To further confirm these identifications, the immunoaffinity enriched peptide mixtures were treated with dithionite, which reduces 3-nitrotyrosine to 3-aminotyrosine. Following reduction, the peptide mixture was analyzed by selectively monitoring for the monoisotopic masses of the unmodified, 3-nitrotyrosine and 3-aminotyrosine containing peptides of the two dominant modified sequences (peptides 284-298 and 416-428). This analysis revealed the presence of unmodified peptides, and peptides with increased masses of +15 amu NYCGLPGE[NH$_2$Y]WLGNDK (SEQ ID NO: 6) and YYWGGQ[NH$_2$Y]TWDMAK (SEQ ID NO: 7)) indicating the presence of 3-aminotyrosine derived from the reduction of 3-nitrotyrosine. Typical spectra of these two peptides before and after reduction with dithionite are shown in FIG. 11C-F. Together the data indicate that the predominant sites of fibrinogen nitration in vivo are residues 292 and 422 in the carboxyl terminus of β-chain. Monoclonal antibodies to the peptides N-Y-C-G-L-P-G-E-[NO$_2$Y]-W-L-G-N-D-K (SEQ ID NO: 2) and Y-Y-W-G-G-Q-[NO$_2$Y]-T-W-D-M-A-K (SEQ ID NO: 3) may be used for detecting nitrated fibrinogen in patients and diagnosing coronary artery disease.

Effect of Fibrinogen Nitration on Fibrin Clot Formation.

Figure 12:
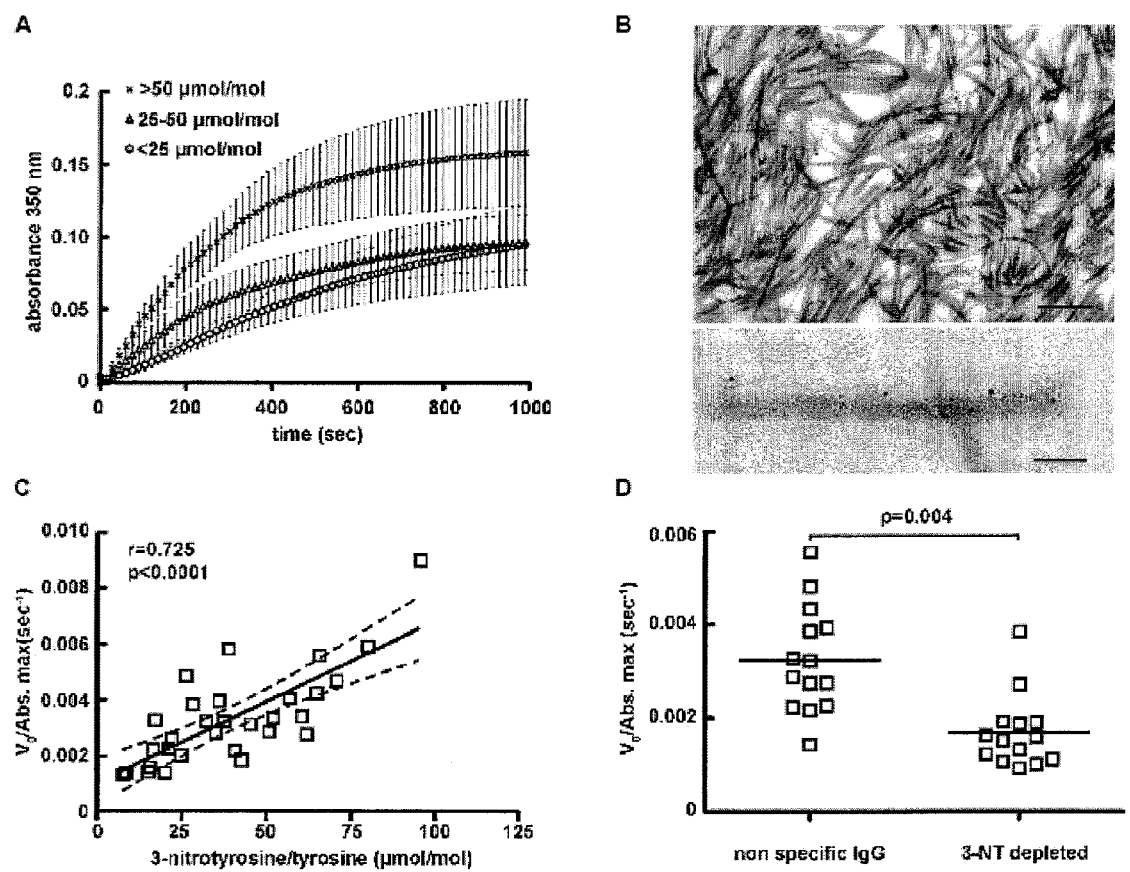
FIG. 12. Fibrinogen nitration accelerates fibrin clot formation. Panel A: Polymerization curves represent the mean±SEM, n=10 subjects per group. Panel B: Representative immuno-EM image of fibrin fibers labeled with anti-nitrotyrosine antibodies and 10 nm protein gold, bar 500 nm (top). Higher magnification of single fibers (bottom) showing the distinctive fibrin band pattern and labeling with anti-nitrotyrosine antibodies, bar 200 nm. Panel C: The initial velocity $V_0$ of each separate curve, normalized for the final turbidity ($V_0$/Abs. max) was plotted against the 3-nitrotyrosine/tyrosine ratio. Spearman analysis reveals a positive correlation between $V_0$/Abs max and 3-nitrotyrosine/tyrosine ratio (r=0.725, p<0.0001, n=30). Panel D: Polymerization assays after immunodepletion. Paired t-test statistical analysis showed a marked reduction of the $V_0$/Abs. max(sec$^{-1}$) after immunodepletion with the anti-nitrotyrosine immunoglobulin (p=0.0004, n=14). The bar indicates the mean value of each group.

To explore the functional consequences of nitration, fibrinogen was isolated from 30 individuals, both controls and smokers in order to represent the entire spectrum of 3-nitrotyrosine levels (ranging from 0-108 μmol 3-nitrotyrosine/mol tyrosine). The quality of the preparation was assessed by SDS-PAGE (FIG. 11a). The samples were then divided into 3 groups based on the levels of fibrinogen nitration; levels <25 μmol 3-nitrotyrosine/mol tyrosine, levels between 25-50 μmol 3-nitrotyrosine/mol tyrosine, and levels >50 μmol 3-nitrotyrosine/mol tyrosine. Ex vivo polymerization was initiated by the addition of 1 NIH U/ml human α-thrombin. As shown in FIG. 12A, polymerization curves of fibrinogen samples with levels >50 μmol 3-nitrotyrosine/mol tyrosine exhibited a steeper increase in absorbance and a higher final turbidity as compared to samples with moderate, 25-50 μmol 3-nitrotyrosine/mol tyrosine and low <25 μmol 3-nitrotyrosine/mol tyrosine levels. Using previously characterized affinity purified anti-nitrotyrosine antibodies and immuno-electron microscopy it was confirmed that nitrated fibrinogen molecules were incorporated in the fibrin fibers (FIG. 12B).

The initial velocity $V_0$ of fibrin clot formation normalized for the maximum absorbance ($V_0$/Abs max) showed a positive correlation with the 3-nitrotyrosine levels (Spearman's r=0.725, p<0.0001, FIG. 12C). Nitration levels were also positively associated with the initial velocity $V_0$ (Spearman's r=0.35, p=0.05), but not with the final turbidity (Spearman's r=0.24, p=0.25). The inclusion of 2.5 mM calcium exhibited the same accelerated kinetics and increased final clot turbidity in samples of purified fibrinogen with >50 μmol 3-nitrotyrosine/mol tyrosine compared to samples with low nitration levels. The same effect was also evident when fibrin clots were made in whole plasma in place of isolated fibrinogen (Spearman's r=0.43, p=0.03, n=23).

Two different approaches were applied to evaluate the contribution of 3-nitrotyrosine to the altered kinetics of fibrin clot formation. Fibrinogen samples were depleted of nitrated fibrinogen molecules by affinity capturing. Aliquots of the same fibrinogen preparations underwent the same procedure using non-specific immunoglobulin to eliminate any interference from sample handling. Elimination of nitrated fibrinogen molecules decreased the initial velocity of clot formation as compared to the nonspecific immunoglobulin for identical fibrinogen concentrations (FIG. 12D). Alternatively, the clotting assay was performed using either isolated fibrinogen or plasma in the presence of the polyclonal anti-nitrotyrosine antibodies or non-specific rabbit immunoglobulin. Inclusion of the specific anti-nitrotyrosine antibody reduced the initial rate of fibrin clot formation compared with the non-specific IgG in both isolated fibrinogen (p=0.001, n=12) and whole plasma (p=0.016, n=22).

Effects of Fibrinogen Nitration on Fibrin Clot Architecture

Figure 13:
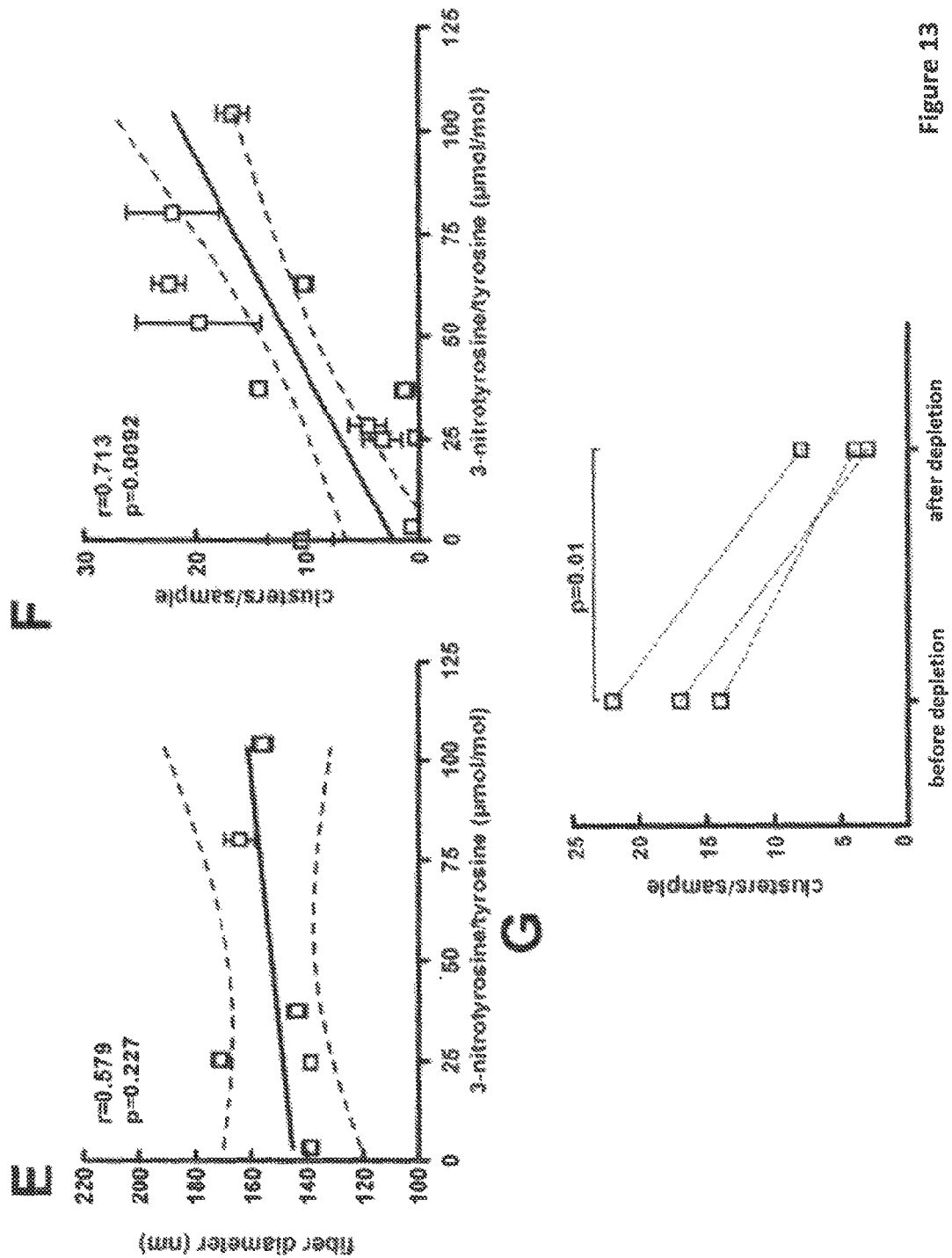
FIG. 13. Scanning electron microscopy (SEM) of fibrin clots. Panel A-C: sample with 3-nitrotyrosine/tyrosine ratio 80.2, 37, 3.3 μmol/mol respectively. Panel D: image from the same sample as in panel A after immunoaffinity depletion of nitrated molecules. Panel E: Fiber diameter is independent of levels of fibrinogen nitration. Panel F: Correlation between fibrin clot cluster formation and fibrinogen nitration levels. Spearman's r=0.713, p=0.0092, n=12. Panel G: Removal of tyrosine nitrated molecules by immunoaffinity depletion results in fibrin clots with significantly decreased number of clusters (p=0.01, n=3). Bar=20 μm.

The effect of tyrosine nitration on clot morphology was investigated by scanning electron microscopy (SEM). Two features of the SEM images were noticeably different in the fibrin clots made from fibrinogen with levels >50 µmol 3-nitrotyrosine/mol tyrosine; the presence of clusters of fibrin and the presence of fibrin bundles. These features are not apparent in fibrin clots with low 3-nitrotyrosine levels, which appear dense and homogenous (FIG. 13C). Clusters and bundles were counted in fibrin clots from 12 different samples with fibrinogen nitration values ranging from 0-104 µmol 3-nitrotyrosine/mol tyrosine. A cluster structure formed by more than 8 single fibers crossing at a single point was defined. The fibers depart the cluster as single fibers and continue in separate directions, thereby forming a well-defined cluster, which appears as a bright spot in the image (FIG. 13A, arrows). Six images per sample under 1000× magnification were selected randomly and clusters were manually counted. Each measurement was repeated for 3 consecutive days and the average of number of clusters per sample was plotted against fibrinogen nitration levels. A significant correlation between the number of clusters per sample and fibrinogen nitration level (Spearman's r=0.70, p=0.01) was revealed (FIG. 13F). Bundles of two or more fibers that are intertwined or run close and parallel to one another for at least the length of one entire 10 $cm^2$ box placed on the 1000× magnified image were also defined. The presence of two or more clearly discernable and separate fibers that are in close proximity did not correlate with the levels of nitrated fibrinogen (r=0.18, p=0.57). Since final turbidity directly relates to the thickness of the fibrin fibers, the thickness of individual fibers was also quantified. Fiber diameters of approximately 150 fibers per image were measured from 5 images per clot in 6 randomly selected clots. The diameter of individual fibrin fibers did not vary as a function of 3-nitrotyrosine content (r=0.58, p=0.23) (FIG. 13E). Scanning electron micrographs of fibrin clots made from isolated fibrinogen after depletion of nitrated fibrinogen molecules were examined to ascertain the role of fibrinogen nitration on the architecture of the fibrin clots. Removal of nitrated fibrinogen molecules resulted in formation of fibrin clots with significantly reduced fiber clustering (FIG. 13G).

Figure 14:
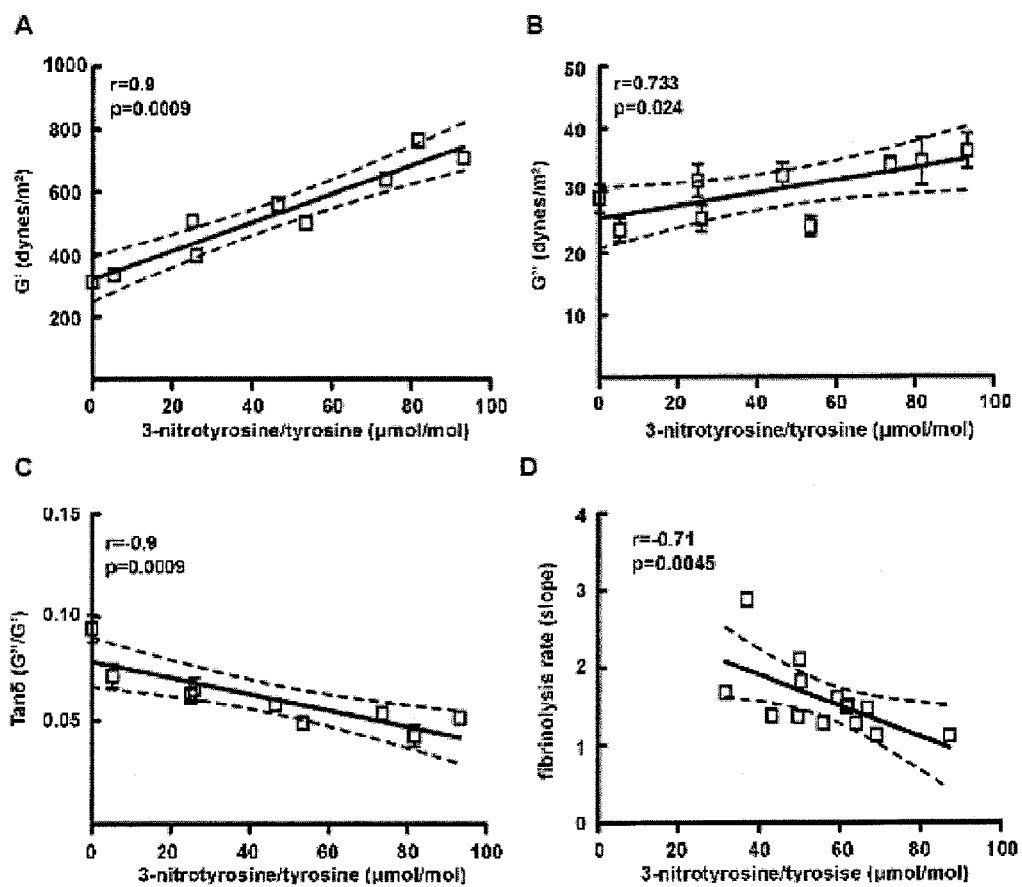
FIG. 14. Viscoelastic properties of fibrin clots. Panel A: Correlation between the G' value (clot stiffness) and 3-nitrotyrosine levels (Spearman r=0.95, p<0.0001, n=9). Panel B: Correlation between the storage module G" (clot plasticity) with the 3-nitrotyrosine burden (Spearman r=0.733, p=0.02, n=9). Panel C: Tan δ (G"/G') association with 3-nitrotyrosine/tyrosine ratio (Spearman r=−0.9, p=0.0009, n=12). The G' and G" values of each separate clot were measured in triplicate. Panel D: Fibrinolytic rate is negatively associated with 3-nitrotyrosine levels in fibrin clots (Spearman's r=−0.71, p=0.0045, n=14).

Effect of Fibrinogen Nitration on Fibrin Clot Viscoelastic Properties and Fibrinolysis The physical properties of fibrin clots were determined by measurement of both the elastic and inelastic parameters in nine different clots. A positive correlation between changes in the storage modulus G', which reflects clot stiffness, with the 3-nitrotyrosine levels of fibrinogen (r=0.9, p=0.0009) were observed (FIG. 14A). Similarly changes in the loss module G", which indicates clot plasticity were positively correlated with the 3-nitrotyrosine levels of fibrinogen (r=0.733, p=0.024) (FIG. 14B). The loss tangent tan δ calculated from the ratio G"/G', which indicates the ratio of energy lost to energy stored in a cyclic deformation declined exponentially when plotted against the levels of 3-nitrotyrosine in fibrinogen. This association is primarily derived by the relatively large increase in the G' values as a function of fibrinogen nitration (FIG. 14C). Moreover, higher nitration levels were associated with lower plasmin-induced fibrinolysis rates (FIG. 14D), whereas fibrinogen degradation products were similar among samples with different nitration levels.

Effect of Nitration on Fibrin Polymerization in the Presence of Knob "B" Mimetic Peptides.

Figure 15:
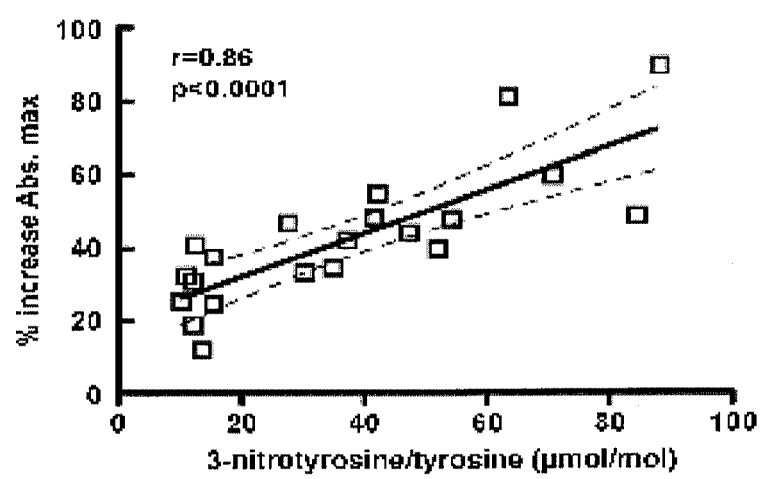
FIG. 15. Positive association between the response to the knob "B" mimetic peptide Gly-His-Arg-Pro$^{am}$ (SEQ ID NO: 9) and fibrinogen nitration levels (Spearman's r=0.86, p<0.0001, n=21). The response to the mimetic peptide was assessed by the percentage increase in final turbidity compared to the baseline (final turbidity in the absence of the peptide).

The mass spectrometric analysis revealed that the modified tyrosine moieties reside on the carboxyl terminal of fibrinogen β-chain, in close proximity to the backbone ridge of the hole "b" (17). The amino acid sequence Gly-His-Arg on the N-terminal of the β-chain interacts with a pocket on the C-terminal of the β-chain (18) and appears to enhance lateral aggregation (19). The observed effect of 3-nitrotyrosine formation on fibrinogen lateral aggregation, which features the effect of knob "B" mimetic peptides, along with the localization of the modified residues suggested that tyrosine nitration might accelerate fibrinogen clotting by means of enhancement of knob "B":hole "b" interactions. To explore this hypothesis, fibrinogen was isolated from 21 plasma samples and polymerization was initiated with the addition of 0.1 U/mL α-thrombin in 3 µM fibrinogen solution in the absence or presence of 250 µM of the knob "B" mimetic peptide GHRPam. The presence of the peptide accelerated the lateral aggregation in all samples. However, the response to the mimetic peptide, assessed by the percent increase in the final turbidity, exhibited a significant correlation with the 3-nitrotyrosine levels (Spearman's r=0.86, p<0.0001) (FIG. 15). Similar results were obtained when polymerization assays were performed with the knob "B" specific (17) peptide AHRPam (Spearman's r=0.56, p=0.035). The data suggest that the presence of tyrosine nitration might induce conformational changes that may facilitate the knob "B":hole "b" interactions.

Discussion

Cigarette smoking has been shown to increase the circulating levels of fibrinogen and smokers have a higher risk for cardiovascular disease and thrombotic events (20,21). Oxidative stress has been considered as one of the mechanisms responsible for the development and progression of cardiovascular and pulmonary disorders and is increased, as reflected by indices of lipid peroxidation, in otherwise apparently healthy smokers (22,23). Moreover, protein tyrosine nitration has been considered one of the posttranslational modifications derived from the reaction of nitric oxide-derived oxidants with proteins.

The current example provides direct experimental evidence to indicate that tyrosine nitration of fibrinogen may account for the increased thrombotic tendency observed under conditions of oxidative stress. Using enrichment strategies and mass spectrometry the sites of in vivo nitration were localized at 2 specific tyrosine residues, Tyr292 and Tyr422 on the beta chain among the 134-tyrosine residues in a fibrinogen molecule. This selectivity of tyrosine nitration (24) could explain the consistent effect of tyrosine nitration on fibrin clot formation. If nitration of fibrinogen occurred at random, then one would observe variable effects, if any, on the function of the protein. However, in this case the effect of tyrosine nitration is consistent and is characterized by the acceleration of lateral aggregation of fibrin molecules. Ex vivo studies revealed significant correlation between the levels of fibrinogen nitration and the velocity of fibrin clot formation, whereas specific elimination of the nitrated fibrinogen molecules restored the kinetics of fibrin clot formation.

These results support a functional consequence of tyrosine nitration on fibrin polymerization in the form of "gain of function" rather than "loss of function", which is typically observed in the oxidatively damaged proteins, including oxidized fibrinogen (8,25,26). Taken together with previously published in vitro studies, which showed that the effects of tyrosine nitration are not replicated by oxidation of fibrinogen (8), the data implicated fibrinogen nitration as a causative modification that may significantly impact normal homeostasis.

These profound effects on fibrin clot structure were produced by a relative small fraction of fibrinogen molecules which had been modified by nitration, which based on two primary sites of nitration, represent 0.6-6% of the β-chain per molecule of fibrinogen. Kinetic analysis of fibrin formation revealed that nitration influences the lateral aggregation, an event that follows the initial fibrinopeptide cleavage, oligomerization and the formation of half-staggered, double stranded protofibrils. It is likely that in the organized assembly of fibrin molecules addition of a molecule with nitrated tyrosine residues accelerates the association of the knob "B": hole "b" interactions, since the two sites of nitration are within the hole "b" of the β-chain. The knobs "B" are exposed after B fibrinopeptide release and engage the hole "b" in the carboxyl terminus of the n-chain during lateral aggregation. The amino acid sequence Gly-His-Arg on the N-terminal of the n-chain interacts with a pocket on the C-terminal of the β-chain and appears to enhance lateral aggregation (19). The location of the tyrosine-modified residues suggested that 3-nitrotyrosine formation might accelerate lateral aggregation by enhancing the knob "B":hole "b" interactions. To explore this, clotting assays were performed in the presence or absence of knob "B" mimetic peptides Gly-His-Arg-Pro$^{am}$ (SEQ ID NO: 9) and Ala-His-Arg-Pro$^{am}$ (SEQ ID NO: 10). The former, which is considered the prototypical knob "B" mimetic, has been shown to interact to a minor extent with the hole "γ" as well (27), while the latter has been shown to be hole "b" specific (17). Interestingly, the response of fibrinogen polymerization to the knob "B" mimetic peptides, assessed by the percent increase in the final turbidity, exhibited a positive correlation with the 3-nitrotyrosine levels. The data suggest that the presence of tyrosine nitration might induce conformational changes that facilitate the knob "B": hole "b" interactions. An alternative plausible explanation for the effect of nitration relates to the location of Tyr422. This residue is located in close proximity to the coiled-coil connecting the middle and ends of the fibrinogen molecule. Nitration of Tyr422 could affect the stability of the interaction between BbAsp398 and AaLys157 that is thought to be responsible for anchoring the C-terminal n-chain to the coiled-coil in fibrinogen. This bond is broken and there is a conformational change of the C-terminal β-chain upon binding of Gly-His-Arg-Pro$^{am}$ (SEQ ID NO: 9) peptide in hole "b". Thus, there are potentially direct links between nitration of these tyrosine residues and the function of this region of fibrinogen in lateral aggregation, although detailed structural effects of nitration of these residues require further investigation.

The mechanical properties of fibrin clots are different in individuals with premature thrombotic events compared to healthy controls (28-32). It has also been suggested that these differences might influence the occurrence of thrombotic events. For example, fibrin clot stiffness, which was associated with reduced fibrinolytic rates, was found to be an independent predictor of premature atherothrombotic events (30). Despite these intriguing associations, the biochemical reasons for the altered mechanical properties remain unknown.

In this example, it is demonstrated that fibrin clot properties are strongly affected by the presence of tyrosine nitrated molecules. Further, a positive association between the levels of fibrinogen nitration accelerated kinetics and clot stiffness as well as a negative association between levels of fibrinogen nitration and the rate of clot lysis is shown. Altered fibrin clot architecture, which was restored upon removal of tyrosine-nitrated molecules was also demonstrated; this is compatible with a role for fibrinogen tyrosine nitration as a causative factor in the increased thrombotic tendency that pertains in smokers, a human model of inflammation and oxidant stress.

The following materials and methods were used to facilitate the practice of this example.

Subjects—Subjects were between 18 and 45 years of age, with a sex and race distribution reflective of the US population. They were in good health; in particular, they had no risk factors for cardiovascular disease other than smoking. Smokers had a history of 4-20 years of smoking. They were classified as heavy smokers if the smoked 11-20 cigarettes/day. Non-smokers had a lifetime consumption of less than 20 cigarettes and lived and worked in a smoke-free environment. Subjects were not on chronic medications (including aspirin, NSAIDS, multivitamins or herbal preparations). However, the oral contraceptive pill, anti-histamines and acid suppressants were permitted. Smokers followed a smoking schedule typical of the number of cigarettes (11-20) for at least 14 months and over a 12-hour monitored period in the General Clinical Research Center prior to the collection of blood. Blood samples were collected 1 hour after the last cigarette in citrate tubes. Plasma was rapidly collected and stored at −80° C. Compliance was confirmed biochemically by measurement of urinary cotinine. The protocols for all clinical studies were scrutinized and approved by the Institutional Review Board.

Quantification of fibrinogen nitration—An ELISA was used to quantify the extent of fibrinogen nitration in plasma, using a polyclonal anti-nitrotyrosine antibody to coat the plate and a polyclonal anti-human fibrinogen antibody conjugated with HRP to detect bound fibrinogen. The ELISA was validated using 3-nitrotyrosine quantification in affinity purified fibrinogen from human plasma by stable isotope dilution ESI/LC/MS/MS (9). Bland-Altman analysis showed a sound agreement between the 2 methods; the average difference between the two methods was only 0.03±2.6 μmol/mol. The data are expressed as the ratio of 3-nitrotyrosine/tyrosine to normalize for variations in fibrinogen plasma concentration.

Fibrinogen isolation—Fibrinogen was isolated from human plasma by glycine precipitation as described previously (10). The pellets were reconstituted with 200 μL 50 mM Tris, 140 mM NaCl pH 7.4 and fibrinogen concentration was determined by BCA protein assay (Pierce, Rockford, Ill.) using fibrinogen as the standard (American Diagnostica, Stamford, Conn.).

Fibrinogen polymerization and fibrinolysis assays—These assays were performed as described previously (8) with minor modification and are described below. Clotting assays were performed in 100 μl glass cells. Fibrinogen concentration was adjusted to 0.5 mg/ml with 50 mM Tris, 140 mM NaCl pH 7.4 and the solution was equilibrated at 37° C. Polymerization was initiated by the addition of human α-thrombin (American Diagnostica, Stamford, Conn.) to a final concentration of 1 NIH U/ml and clot formation was monitored by the increase in absorbance at 350 nm using a Hewlett-Packard diode array spectrophotometer. The initial velocity $V_0$ of clot formation was calculated by the slope of the curve immediately after the lag phase. Polymerization in the presence of calcium was performed with 1 mg/ml fibrinogen in TBS containing 2.5 mM CaCl$_2$ after addition of 1 NIH U/ml human α-thrombin.

The clotting assays after non-specific and 3-nitrotyrosine immunodepletion and those in the presence of non-specific and anti-nitrotyrosine antibody were performed in 96 well plates. For these assays, 100 μg of fibrinogen were diluted in 180 μL TBS, followed by the simultaneous addition of 20 μl α-thrombin to a final activity of 0.1 NIH U/ml. Plasma clotting experiments were also performed in 96 well plates. Plasma fibrinogen was adjusted to 1.5 mg/ml with TBS and clotting was initiated by the simultaneous addition of 0.1 U/ml human α-thrombin and 10 mM CaCl$_2$. Clotting in the presence of mimetic peptides Gly-His-Arg-Pro$^{am}$ (SEQ ID NO: 9) and Ala-His-Arg-Pro$^{am}$ (SEQ ID NO: 10) (synthesized by CPC scientific, San Jose, Calif.) was performed in 96 well plates with 1 mg/mL fibrinogen 250 μM peptide, and 0.1 U/ml thrombin.

For fibrinolysis, 1.0 mg/mL fibrinogen was polymerized with 0.1 U/mL α-thrombin in 96 well plates. Seven hundred (700) nM glu-Plasminogen (American Diagnostica, Stamford, Conn.) and 70 nM tissue plasminogen activator (EMD Chemicals, Gibbstown, N.J.) in TBS were added on the top of the clots and absorbance at 350 nm for 3 hours was recorded. Lysis rate was calculated by the slope in the latter part of the curve. The plasmin-induced fibrinogen degradation products were collected and analyzed in 10% SDS-PAGE under non-reducing conditions.

Immunodepletion of nitrated fibrinogen—Nitrated fibrinogen was isolated using the polyclonal anti-nitrotyrosine antibodies described elsewhere (11). The antibodies were covalently coupled to aminolink plus agarose beads (Pierce, Rockford, Ill.). Isolated fibrinogen (200 μg total protein for nitrotyrosine depletion experiments and 500 μg for mass spectrometry) dissolved in 400 μL of 50 mM Tris, 140 mM NaCl pH 7.4 was incubated overnight with the beads at 4° C. The samples were then centrifuged at 3,000 g for 3 min and the flow through, which contained the nitrotyrosine depleted fibrinogen, was used for polymerization assays. The beads were washed with 10 column volumes of TBS. The nitrated fibrinogen was eluted with 0.1 M glycine pH 2.7, concentrated to a small volume using YM-10 microcon filters (Millipore, Billerica, Mass.) and used for Western blot experiments or trypsinized for mass spectrometry. Because the nitrotyrosine immuno-depletion required handling that could alter the fibrinogen polymerization properties, aliquots of isolated fibrinogen were also processed through the same procedure in beads linked to non-specific immunoglobulin.

Peptide capture—Fibrinogen (500 μg) was digested as described elsewhere (12). Antinitrotyrosine antibodies were added to the peptide mixture (antibody to protein ratio 1:25) and were incubated overnight at 4° C. The mixture was transferred into a 10 kD MWCO filter, washed with 5 volumes of PBS, 5 volumes of 0.5 M NaCl and finally 3 volumes of water. The bound peptides were eluted with 1 M formic acid/10% ACN, concentrated and analyzed by LC/ESI/MS/MS.

Gels and western blotting—Samples were separated in 10% tris-glycine or 4-12% bis-tris gradient gels (Invitrogen, Carlsbad, Calif.) and stained with colloidal blue (Invitrogen, Carlsbad, Calif.) or transferred to a PVDF membrane and probed with anti-nitrotyrosine or polyclonal anti-human fibrinogen antibodies (DAKO, Carpinteria, Calif.). Band intensities where quantified using the Odyssey software v1.2 (LI-COR, Lincoln, Nebr.).

Mass spectrometry and MS/MS spectra evaluation—Samples were analyzed with a LTQ linear ion trap instrument (Thermo Electron, San Jose, Calif.) as described elsewhere (13,14). High resolution LC/MS/MS of the nitrated peptides were analyzed with an LTQ-Orbitrap hybrid instrument (Thermo Fisher, Bremen, Germany) equipped with an Eksigent 1Dplus nanoLC and autosampler (Eksigent, Dublin, Calif.). One full MS scan from 400-2000 m/z at a resolution of 60,000 was acquired followed by data-dependent acquisition of MS/MS scans as previously described (13,14). In separate experiments, the one full MS scan from 400-2000 m/z at a resolution of 60,000 was followed by the acquisition of MS/MS in a targeted fashion collecting MS/MS spectra for the specific m/z values 864.86, 842.86, 842.37, 850.36, 857.35, 865.35, 893.38, 900.89, and 915.89. MS/MS spectra were collected using an isolation width of 2 m/z, an activation time of 30 ms, and activation Q of 0.250 and 35% normalized collision energy using 1 microscan and maximum injection time of 100 for each scan. The mass spectrometer was tuned prior to analysis using the synthetic peptide TpepK (AVAGKAGAR) (SEQ ID NO: 8). Typical tune parameters were as follows: spray voltage of between 1.8 KV, a capillary temperature of 150° C., a capillary voltage of 50V and tube lens 100V. Peptide sequences matched to MS/MS spectra by Sequest were accepted based on the selection criteria described previously (14,15).

Immuno-electron microscopy, scanning electron microscopy and viscoelastic properties of clots—These experiments were performed as described previously (11,15,16).

REFERENCES

1. Mosesson M W. Fibrinogen and fibrin structure and functions. *J Thromb Haemost.* 2005; 3:1894-1904.
2. Prandoni P, Bilora F, Marchiori A, Bernardi E, Petrobelli F, Lensing A W, Prins M H, Girolami A. An association between atherosclerosis and venous thrombosis. *N. Engl. J Med.* 2003; 348:1435-1441.
3. Rosenberg R D, Aird W C. Vascular-bed—specific hemostasis and hypercoagulable states. *N Engl J Med.* 1999; 340:1555-1564.
4. Alpert J S, Smith R, Carlson J, Ockene I S, Dexter L, Dalen J E. Mortality in patients treated for pulmonary embolism. *JAMA.* 1976; 236:1477-1480.
5. Ferro D, Pittoni V, Quintarelli C, Basili S, Saliola M, Caroselli C, Valesini G, Violi F. Coexistence of anti-phospholipid antibodies and endothelial perturbation in systemic lupus erythematosus patients with ongoing prothrombotic state. *Circulation.* 1997; 95:1425-1432.
6. Thompson S G, Kienast J, Pyke S D, Haverkate F, van de Loo J C. Hemostatic factors and the risk of myocardial infarction or sudden death in patients with angina pectoris. European Concerted Action on Thrombosis and Disabilities Angina Pectoris Study Group. *N Engl J Med.* 1995; 332:635-641.
7. Kannel W B, Wolf P A, Castelli W P, D'Agostino R B. Fibrinogen and risk of cardiovascular disease. The Framingham Study. *Jama.* 1987; 258:1183-1186.
8. Vadseth C, Souza J M, Thomson L, Seagraves A, Nagaswami C, Scheiner T, Torbet J, Vilaire G, Bennett J S, Murciano J C, Muzykantov V, Penn M S, Hazen S L, Weisel J W, Ischiropoulos H. Pro-thrombotic state induced by posttranslational modification of fibrinogen by reactive nitrogen species. *J Biol. Chem.* 2004; 279:8820-8826.
9. Brennan M L, Wu W, Fu X, Shen Z, Song W, Frost H, Vadseth C, Narine L, Lenkiewicz E, Borchers M T, Lusis A J, Lee J J, Lee N A, Abu-Soud H M, Ischiropoulos H, Hazen S L. A tale of two controversies: defining both the role of peroxidases in nitrotyrosine formation in vivo using eosinophil peroxidase and myeloperoxidase-deficient mice, and the nature of peroxidase-generated reactive nitrogen species. *J Biol. Chem.* 2002; 277:17415-17427.
10. Kazal L A, Amsel S, Miller O P, Tocantins L M. The Preparation and Some Properties of Fibrinogen Precipitated from Human Plasma by Glycine. *Proc Soc Exp Biol Med.* 1963; 113:989-994.
11. Heijnen H F, van Donselaar E, Slot J W, Fries D M, Blachard-Fillion B, Hodara R, Lightfoot R, Polydoro M, Spielberg D, Thomson L, Regan E A, Crapo J, Ischiropoulos H. Subcellular localization of tyrosine-nitrated proteins is dictated by reactive oxygen species generating enzymes and by proximity to nitric oxide synthase. *Free Radic Biol Med.* 2006; 40:1903-1913.
12. Manza L L, Stamer S L, Ham A J, Codreanu S G, Liebler D C. Sample preparation and digestion for proteomic analyses using spin filters. *Proteomics.* 2005; 5:1742-1745.
13. Greco T M, Hodara R, Parastatidis I, Heijnen H F, Dennehy M K, Liebler D C, Ischiropoulos H. Identification of S-nitrosylation motifs by site-specific mapping of the S-nitrosocysteine proteome in human vascular smooth muscle cells. *Proc Natl Acad Sci USA.* 2006; 103:7420-7425.
14. Parastatidis I, Thomson L, Fries D M, Moore R E, Tohyama J, Fu X, Hazen S L, Heijnen H F, Dennehy M K, Liebler D C, Rader D J, Ischiropoulos H. Increased Protein Nitration Burden in the Atherosclerotic Lesions and Plasma of Apolipoprotein A-I-Deficient Mice. *Circ Res.* 2007; 101:368-376.
15. Weisel J W, Nagaswami C. Computer modeling of fibrin polymerization kinetics correlated with electron microscope and turbidity observations: clot structure and assembly are kinetically controlled. *Biophys J.* 1992; 63:111-128.
16. Ryan E A, Mockros L F, Weisel J W, Lorand L. Structural origins of fibrin clot rheology. *Biophys J.* 1999; 77:2813-2826.
17. Doolittle R F, Chen A, Pandi L. Differences in binding specificity for the homologous gamma- and beta-chain "holes" on fibrinogen: exclusive binding of Ala-His-Arg-Pro-amide by the beta-chain hole. *Biochemistry.* 2006; 45:13962-13969.
18. Litvinov R I, Gorkun O V, Galanakis D K, Yakovlev S, Medved L, Shuman H, Weisel J W. Polymerization of fibrin: Direct observation and quantification of individual B:b knob-hole interactions. *Blood.* 2007; 109:130-138.
19. Weisel J W, Veklich Y, Gorkun O. The sequence of cleavage of fibrinopeptides from fibrinogen is important for protofibril formation and enhancement of lateral aggregation in fibrin clots. *J Mol. Biol.* 1993; 232:285-297.
20. Kannel W B, D'Agostino R B, Belanger A J. Fibrinogen, cigarette smoking, and risk of cardiovascular disease: insights from the Framingham Study. *Am Heart J.* 1987; 113:1006-1010.
21. Dotevall A, Kutti J, Teger-Nilsson A C, Wadenvik H, Wilhelmsen L. Platelet reactivity, fibrinogen and smoking. *Eur J. Haematol.* 1987; 38:55-59.
22. Reilly M, Delanty N, Lawson J A, FitzGerald G A. Modulation of oxidant stress in vivo in chronic cigarette smokers. *Circulation.* 1996; 94:19-25.
23. Morrow J D, Frei B, Longmire A W, Gaziano J M, Lynch S M, Shyr Y, Strauss W E, Oates J A, Roberts L J, 2nd. Increase in circulating products of lipid peroxidation (F2-isoprostanes) in smokers. Smoking as a cause of oxidative damage. *N Engl J Med.* 1995; 332:1198-1203.
24. Gow A J, Farkouh C R, Munson D A, Posencheg M A, Ischiropoulos H. Biological significance of nitric oxide-mediated protein modifications. *Am J Physiol Lung Cell Mol. Physiol.* 2004; 287:L262-268.
25. Inada Y, Hessel B, Blomback B. Photooxidation of fibrinogen in the presence of methylene blue and its effect on polymerization. *Biochim Biophys Acta.* 1978; 532:161-170.
26. Shacter E, Williams J A, Levine R L. Oxidative modification of fibrinogen inhibits thrombin-catalyzed clot formation. *Free Radic Biol Med.* 1995; 18:815-821.
27. Everse S J, Spraggon G, Veerapandian L, Doolittle R F. Conformational changes in fragments D and double-D from human fibrin(ogen) upon binding the peptide ligand Gly-His-Arg-Pro-amide. *Biochemistry.* 1999; 38:2941-2946.
28. Fatah K, Hamsten A, Blomback B, Blomback M. Fibrin gel network characteristics and coronary heart disease: relations to plasma fibrinogen concentration, acute phase protein, serum lipoproteins and coronary atherosclerosis. *Thromb Haemost.* 1992; 68:130-135.
29. Fatah K, Silveira A, Tornvall P, Karpe F, Blomback M, Hamsten A. Proneness to formation of tight and rigid fibrin gel structures in men with myocardial infarction at a young age. *Thromb Haemost.* 1996; 76:535-540.
30. Collet J P, Allali Y, Lesty C, Tanguy M L, Silvain J, Ankri A, Blanchet B, Dumaine R, Gianetti J, Payot L, Weisel J W, Montalescot G. Altered fibrin architecture is associated with hypofibrinolysis and premature coronary athero-thrombosis. *Arterioscler Thromb Vasc Biol.* 2006; 26:2567-2573.
31. Gurbel P A, Bliden K P, Guyer K, Cho P W, Zaman K A, Kreutz R P, Bassi A K, Tantry U S. Platelet reactivity in patients and recurrent events post-stenting: results of the PREPARE POST-STENTING Study. *J Am Coll Cardiol.* 2005; 46:1820-1826.
32. Mills J D, Ariens R A, Mansfield M W, Grant P J. Altered fibrin clot structure in the healthy relatives of patients with premature coronary artery disease. *Circulation.* 2002; 106:1938-1942.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining the presence or risk for coronary artery disease or risk for increased propensity for an adverse thrombotic event in a patient, said method comprising:

a) obtaining a sample of blood or fraction thereof from the patient;

b) determining by immunoassay the amount of fibrinogen β-chain nitrated at position 292 in said sample by contacting the sample with an antibody that specifically recognizes SEQ ID NO: 2, wherein the antibody demonstrates binding affinity for fibrinogen to the exclusion of other proteins; and measuring the amount of binding of nitrated fibrinogen to the antibody, thereby determining the amount of fibrinogen β-chain nitrated at position 292;

c) comparing the amount of said fibrinogen β-chain nitrated at position 292 in said sample with the amount of fibrinogen β-chain nitrated at position 292 in a sample from a normal individual; and d) determining the presence or risk for coronary artery disease or risk for increased propensity for an adverse thrombotic event in the patient based upon the compared amounts, wherein a greater amount of said fibrinogen nitrated at position 292 in said sample from said patient than in said normal individual is indicative of the presence of coronary artery disease or of a greater risk of coronary artery disease or of a risk of increased propensity for an adverse thrombotic event in said patient.

2. The method of claim 1, further comprising determining the amount of fibrinogen in said sample in step b) and comparing the ratio of nitrated fibrinogen/fibrinogen in said sample with the ratio of nitrated fibrinogen/fibrinogen in a sample from the normal individual; wherein a greater ratio of nitrated fibrinogen/fibrinogen in said sample from said patient than in said normal individual is indicative of the presence of coronary artery disease or of a greater risk of coronary artery disease in said patient.

3. The method of claim 1, wherein said immunoassay is an ELISA.

4. The method of claim 3, wherein said ELISA is a sandwich ELISA.

5. The method of claim 4, wherein said sandwich ELISA further comprises a detection antibody which recognizes fibrinogen.

6. The method of claim 4, wherein said sandwich ELISA further comprises a capture antibody which recognizes fibrinogen.

7. A method for determining the presence or risk for coronary artery disease or risk for increased propensity for an adverse thrombotic event in a patient, said method comprising:
   a) obtaining a sample of blood or fraction thereof from the patient;
   b) determining by immunoassay the amount of fibrinogen β-chain nitrated at position 422 in said sample by contacting the sample with an antibody that specifically recognizes SEQ ID NO: 3, wherein the antibody demonstrates binding affinity for fibrinogen to the exclusion of other proteins; and measuring the amount of binding of nitrated fibrinogen to the antibody, thereby determining the amount of fibrinogen β-chain nitrated at position 422;
   c) comparing the amount of said fibrinogen β-chain nitrated at position 422 in said sample with the amount of fibrinogen β-chain nitrated at position 422 in a sample from a normal individual; and
   d) determining the presence or risk for coronary artery disease or risk for increased propensity for an adverse thrombotic event in the patient based upon the compared amounts, wherein a greater amount of said fibrinogen nitrated at position 422 in said sample from said patient than in said normal individual is indicative of the presence of coronary artery disease or of a greater risk of coronary artery disease or of a risk of increased propensity for an adverse thrombotic event in said patient.

8. The method of claim 7, further comprising determining the amount of fibrinogen in said sample in step b) and comparing the ratio of nitrated fibrinogen/fibrinogen in said sample with the ratio of nitrated fibrinogen/fibrinogen in a sample from the normal individual; wherein a greater ratio of nitrated fibrinogen/fibrinogen in said sample from said patient than in said normal individual is indicative of the presence of coronary artery disease or of a greater risk of coronary artery disease in said patient.

9. The method of claim 7, wherein said immunoassay is an ELISA.

10. The method of claim 9, wherein said ELISA is a sandwich ELISA.

11. The method of claim 10, wherein said sandwich ELISA further comprises a detection antibody which recognizes fibrinogen.

12. The method of claim 10, wherein said sandwich ELISA further comprises a capture antibody which recognizes fibrinogen.

* * * * *

SEQUENCE LISTING

```
<160> NUMBER OF SEQ ID NOS: 10

<210> SEQ ID NO 1
<211> LENGTH: 8
<212> TYPE: PRT
<213> ORGANISM: human
<220> FEATURE:
```

```
<221> NAME/KEY: VARIANT
<222> LOCATION: (3)...(3)
<223> OTHER INFORMATION: Nitrated tyrosine residue at position 3
<220> FEATURE:
<221> NAME/KEY: VARIANT
<222> LOCATION: (7)...(7)
<223> OTHER INFORMATION: Nitrated tyrosine residue at position 7

<400> SEQUENCE: 1

Cys Gly Tyr Gly Gly Gly Tyr Gly
 1               5

<210> SEQ ID NO 2
<211> LENGTH: 15
<212> TYPE: PRT
<213> ORGANISM: human
<220> FEATURE:
<221> NAME/KEY: VARIANT
<222> LOCATION: (9)...(9)
<223> OTHER INFORMATION: Nitrated tyrosine residue at position 9

<400> SEQUENCE: 2

Asn Tyr Cys Gly Leu Pro Gly Glu Tyr Trp Leu Gly Asn Asp Lys
 1               5                  10                  15

<210> SEQ ID NO 3
<211> LENGTH: 13
<212> TYPE: PRT
<213> ORGANISM: human
<220> FEATURE:
<221> NAME/KEY: VARIANT
<222> LOCATION: (7)...(7)
<223> OTHER INFORMATION: Nitrated tyrosine residue at position 7

<400> SEQUENCE: 3

Tyr Tyr Trp Gly Gly Gln Tyr Thr Trp Asp Met Ala Lys
 1               5                  10

<210> SEQ ID NO 4
<211> LENGTH: 15
<212> TYPE: PRT
<213> ORGANISM: human

<400> SEQUENCE: 4

Asn Tyr Cys Gly Leu Pro Gly Glu Tyr Trp Leu Gly Asn Asp Lys
 1               5                  10                  15

<210> SEQ ID NO 5
<211> LENGTH: 13
<212> TYPE: PRT
<213> ORGANISM: human

<400> SEQUENCE: 5

Tyr Tyr Trp Gly Gly Gln Tyr Thr Trp Asp Met Ala Lys
 1               5                  10

<210> SEQ ID NO 6
<211> LENGTH: 15
<212> TYPE: PRT
<213> ORGANISM: human
<220> FEATURE:
<221> NAME/KEY: VARIANT
<222> LOCATION: (9)...(9)
<223> OTHER INFORMATION: Aminated tyrosine residue at position 9

<400> SEQUENCE: 6

Asn Tyr Cys Gly Leu Pro Gly Glu Tyr Trp Leu Gly Asn Asp Lys
 1               5                  10                  15
```

```
<210> SEQ ID NO 7
<211> LENGTH: 13
<212> TYPE: PRT
<213> ORGANISM: human
<220> FEATURE:
<221> NAME/KEY: VARIANT
<222> LOCATION: (7)...(7)
<223> OTHER INFORMATION: Aminated tyrosine residue at position 7

<400> SEQUENCE: 7

Tyr Tyr Trp Gly Gly Gln Tyr Thr Trp Asp Met Ala Lys
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Ala Val Ala Gly Lys Ala Gly Ala Arg
 1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4

<400> SEQUENCE: 9

Gly His Arg Pro
 1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4

<400> SEQUENCE: 10

Ala His Arg Pro
 1
```